United States Patent [19]

Carson et al.

[11] Patent Number: 5,374,772
[45] Date of Patent: Dec. 20, 1994

[54] SUBSTITUTED BENZOIC ACIDS, INHIBITORS OF PHOSPHOLIPASES A₂

[75] Inventors: Mathew Carson, Nutley; Ru-Jen L. Han, Princeton Junction; Ronald LeMahieu, N. Caldwell; Vincent S. Madison, Mountain Lakes, all of N.J.

[73] Assignee: Hoffmann-LaRoche Inc., Nutley, N.J.

[21] Appl. No.: 141,309

[22] Filed: Oct. 22, 1993

Related U.S. Application Data

[63] Continuation-in-part of Ser. No. 987,227, Dec. 8, 1992, abandoned.

[51] Int. Cl.⁵ .................................. C07C 65/00
[52] U.S. Cl. ........................ 562/473; 560/64;
560/74; 560/53; 560/21; 560/19; 560/18;
562/461; 562/463; 562/427; 562/435; 562/433
[58] Field of Search ............ 562/473, 461, 427, 463,
562/433, 435; 560/53, 64, 74, 21, 19, 18;
514/568, 544, 540, 568

[56] References Cited

U.S. PATENT DOCUMENTS

| | | |
|---|---|---|
| 3,078,314 | 2/1983 | Monniicendam et al. . |
| 4,499,295 | 2/1985 | Mueller et al. . |
| 4,590,291 | 5/1986 | Böshagen et al. .......... 560/64 |
| 4,670,465 | 6/1987 | Guzman et al. . |
| 4,871,712 | 10/1989 | Reinhardt . |
| 5,025,036 | 6/1991 | Carson et al. ............ 514/560 |

FOREIGN PATENT DOCUMENTS

| | | |
|---|---|---|
| 0068250 | 5/1983 | European Pat. Off. . |
| 0310126 | 5/1989 | European Pat. Off. . |
| 2439458 | 2/1975 | Germany . |

OTHER PUBLICATIONS

Franson R; Dobrow R; Weiss J; Elsbach P; and Weglick W. B., J. Lipid Res. 19, 18–23 (1978).
J. M. Yound; B. M. Wagner & D. A. Spires J. Invest. Dermatology 80, 48–52 (1983).
P. P. Bradley; D. A. Priebat, R. D. Christensen & G. Rothstein J. Invest. Dermatology 78, 206–209 (1982).
J. E. Krawisz et al., In Amer. J. Proc. Gastro. Col. Rec. Surg. 31;–11–18 (1980).
P. Sharon & W. F. Stenson, Gastroenterology 88, 55–63, 453–460 (1984).
P. Sharon & W. F. Stenson, Gastroenterology 86, 453–460 (1984).

*Primary Examiner*—Paul J. Killos
*Attorney, Agent, or Firm*—George M. Gould; William G. Isgro

[57] ABSTRACT

The invention relates to compounds of the formula

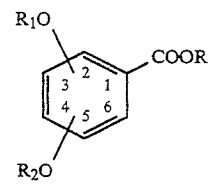

R is hydrogen, lower alkyl, $-(CH_2)_2N(R_3)_2$ or $-CH_2OOCR_3$ wherein $R_3$ is lower alkyl;

$R_1$ is $CH_3(CH_2)_n-$, wherein n is 0–17, or $R_4(CH_2)_p-$, wherein p is 2–18 and $R_4$ is 1- or 2-naphthyloxy, 2,3- or 3,4-dihydroxyphenyl, phenyl, phenoxy, or substituted phenyl or phenoxy wherein the substituent is selected from the group consisting of hydroxy, benzyloxy, methylsulfinyl, methylsulfonyl or phenyl;

$R_2$ is $R_4(CH_2)_p-$, 1-adamantyl—CO— or diphenylmethyl—CO—, and, when R is hydrogen, pharmaceutically acceptable salts with bases.

The compounds of formula I are potent inhibitors of phospholipases A₂ (PLA₂'s) and are therefore useful in the treatment of diseases, such as psoriasis, inflammatory bowel disease, asthma, allergy, arthritis, dermatitis, gout, pulmonary disease, myocardial ischemia, and trauma induced inflammation, such as spinal cord injury.

30 Claims, No Drawings

SUBSTITUTED BENZOIC ACIDS, INHIBITORS OF PHOSPHOLIPASES $A_2$

This application is a Continuation-in-part of Ser. No. 07/987,227, filed Dec. 8, 1992 now abandoned.

BRIEF SUMMARY OF THE INVENTION

The invention relates to compounds of the formula

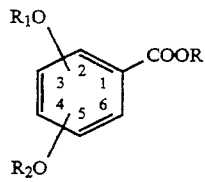

R is hydrogen, lower alkyl, —$(CH_2)_2N(R_3)_2$ or —$CH_2OOCR_3$ wherein $R_3$ is lower alkyl;

$R_1$ is $CH_3(CH_2)_n$—, wherein n is 0–17, or $R_4(CH_2)_p$—, wherein p is 2–18 and $R_4$ is 1- or 2-naphthyloxy, 2,3- or 3,4-dihydroxyphenyl, phenyl, phenoxy, or substituted phenyl or phenoxy wherein the substituent is selected from the group consisting of hydroxy, benzyloxy, methylsulfinyl, methylsulfonyl or phenyl;

$R_2$ is $R_4(CH_2)_p$—, 1-adamantyl—CO— or diphenylmethyl—CO—, and, when R is hydrogen, pharmaceutically acceptable salts with bases.

The compounds of formula 1 are potent inhibitors of phospholipases $A_2$ (PLA2's) and are therefore useful in the treatment of diseases, such as psoriasis, inflammatory bowel disease, asthma, allergy, arthritis, dermatitis, gout, pulmonary disease, myocardial ischemia, and trauma induced inflammation, such as spinal cord injury.

In another aspect, the invention relates to compositions and methods of use comprising the compounds of formula 1.

BACKGROUND OF THE INVENTION

Phospholipases $A_2$ (PLA2's) are a class of enzymes which catalyze the hydrolysis of membrane phospholipids at the sn-2 position leading to free fatty acids and lysophospholipid. Arachidonic acid is stored in the cell membrane as an ester almost exclusively at the 2-position of phospholipids. PLA2 acts to release arachidonic acid from phospholipids in what is believed to be the rate controlling step which ultimately leads to the products of the arachidonic acid cascade. Free arachidonic acid is rapidly metabolized by cyclooxygenase to give prostaglandins and thromboxane or by lipoxygenases to form hydroxy fatty acids and leukotrienes. Prostaglandins and leukotrienes are important mediators of inflammation and hydroxy fatty acids such as leukotriene B4 act as chemotactic agents for neutrophils and eosinophils and may cause cell migration to sites of inflammation. Lysophospholipids are cytotoxic and have also been implicated in several inflammatory conditions. In addition, platelet activating factor (PAF) can be formed by the action of an acetyl transferase on a 1-alkyl-2-lysophospholipid. PAF is a potent platelet aggregating substance and causes various inflammatory conditions such as erythema, vascular permeability and cellular chemotaxis. These facts provide support for the utilization of an inhibitor of PLA2's as therapy for various inflammatory conditions.

DETAILED DESCRIPTION OF THE INVENTION

The invention relates to compounds of the formula

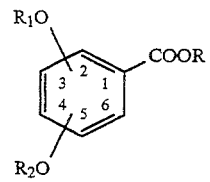

R is hydrogen, lower alkyl, —$(CH_2)_2N(R_3)_2$ or —$CH_2OOCR_3$ wherein $R_3$ is lower alkyl;

$R_1$ is $CH_3(CH_2)_n$—, wherein n is 0–17, or $R_4(CH_2)_p$—, wherein p is 2–18 and $R_4$ is 1- or 2-naphthyloxy, 2,3- or 3,4-dihydroxyphenyl, phenyl, phenoxy, or substituted phenyl or phenoxy wherein the substituent is selected from the group consisting of hydroxy, benzyloxy, methylsulfinyl, methylsulfonyl or phenyl;

$R_2$ is $R_4(CH_2)_p$—, 1-adamantyl—CO— or diphenylmethyl—CO—, and, when R is hydrogen, pharmaceutically acceptable salts with bases.

As used herein, the term "lower alkyl", alone or in combination, denotes a straight or branched chain saturated hydrocarbon containing 1 to 7 carbon atoms, preferably from 1 to 4 carbon atoms, for example, methyl, ethyl, propyl, isopropyl, butyl, dimethylethyl, neopentyl, pentyl, heptyl, and the like.

The preferred compounds of formula 1 can have any of four substitution patterns:

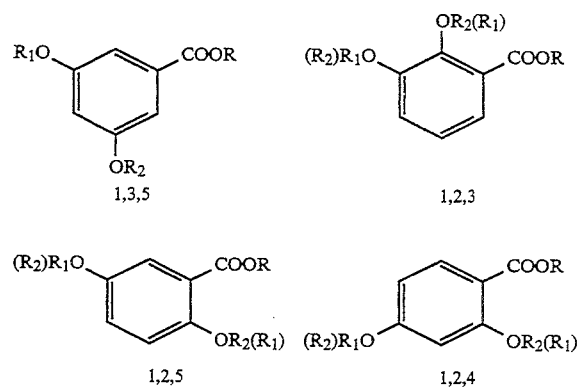

wherein R, $R_1$ and $R_2$ are as previously described.

More preferred compounds of formula 1 are those in which the substitution pattern is 1,3,5 or 1,2,3, preferably 1,3,5;

$R_1$ is $CH_3(CH_2)_n$—, wherein n is 6–17, preferably 9–17;

$R_2$ is 1-adamantyl—CO—, diphenylmethyl—CO—, or $R_4(CH_2)_p$—, wherein p is 3–10 and $R_4$ is 2,3- or 3,4-dihydroxyphenyl or substituted phenoxy wherein the substituent is selected from hydroxy, benzyloxy, methylsulfinyl; and R is as previously described.

The most preferred compounds of formula 1 are those in which the substitution pattern is 1,3,5;

$R_1$ is $CH_3(CH_2)_n$—, wherein n is 9–17;

$R_2$ is $R_4(CH_2)_p$—, wherein p is 3–8 and $R_4$ is 2,3-dihydroxyphenyl or substituted phenoxy wherein the substituent is selected from benzyloxy or hydroxy, and R is hydrogen.

Preferred compounds of the invention are:

3-[[6-(2,3-dihydroxyphenyl)hexyl]oxy]-5-(octadecyloxy)benzoic acid;
3-[3-(4-hydroxyphenoxy)propoxy]-5-(octadecyloxy)benzoic acid;
3-[3-(4-hydroxyphenoxy)propoxy]-5-(tetradecyloxy)benzoic acid;
3-(decyloxy)-5-[3-(4-hydroxyphenoxy)propoxy]benzoic acid:
3-[[6-(2,3-dihydroxyphenyl)hexyl]oxy]-5-(tetradecyloxy)benzoic acid;
3-(decyloxy)-5-[[6-(2,3-dihydroxyphenyl)hexyl]oxy]benzoic acid;
3-(octadecyloxy)-5-(2,2-diphenyl-1-oxoethoxy)benzoic acid;
3-(octadecyloxy)-5-[(tricyclo[3.3.1./3,7/]dec-1-ylcarbonyl)oxy]benzoic acid;
3-(octadecyloxy)-5-(3-phenoxypropoxy)benzoic acid;
3-[[3-(4-phenylmethoxy)phenoxy]propoxy]-5-(octadecyloxy)benzoic acid;
3-[[6-(2,3-dihydroxyphenyl)hexyl]oxy]-5-(octadecyloxy)benzoic acid methyl ester;
3-[3-(4-hydroxyphenoxy)propoxy]-5-(octadecyloxy)benzoic acid methyl ester;
3-[[6-(2,3-dihydroxyphenyl)hexyl]oxy]-5-(tetradecyloxy)benzoic acid methyl ester;
3-(decyloxy)-5-[[6-(2,3-dihydroxyphenyl)hexyl]oxy]benzoic acid methyl ester, and
2-[3-(4-hydroxyphenoxy)propoxy]-3-(octadecyloxy)benzoic acid.

Exemplary of other compounds of the invention are:

3-[3-(4-hydroxyphenoxy)propoxy]-5-(octyloxy)benzoic acid;
3-(dodecyloxy)-5-[3-(4-hydroxyphenoxy)propoxy]benzoic acid;
3-(hexyldecyloxy)-5-[3-(4-hydroxyphenoxy)propoxy]benzoic acid;
3-[4-(4-hydroxyphenoxy)butoxy]-5-(octyloxy)benzoic acid;
3-[4-(4-hydroxyphenoxy)butoxy]-5-(octyloxy)benzoic acid;
3-[[8-(4-hydroxyphenoxy)octyl]oxy]-5-(octyloxy)benzoic acid;
3-[3-(3-hydroxyphenoxy)propoxy]-5-(octyloxy)benzoic acid;
3-[3-(4-phenylphenoxy)propoxy]-5-(octyloxy)benzoic acid;
2-[3-(4-hydroxyphenoxy)propoxy]-3-(tetradecyloxy)benzoic acid;
2-[3-(4-hydroxyphenoxy)propoxy]-3-(hexadecyloxy)benzoic acid;
2-[3-(4-hydroxyphenoxy)propoxy]-3-(decyloxy)benzoic acid;
2-[3-(2-hydroxyphenoxy)propoxy]-3-(tetradecyloxy)benzoic acid;
2-[3-(2-hydroxyphenoxy)propoxy]-3-(octadecyloxy)benzoic acid;
2-[[6-(4-hydroxyphenoxy)hexyl]oxy]-3-(tetradecyloxy)benzoic acid;
2-[[8-(4-hydroxyphenoxy)octyl]oxy]-3-(tetradecyloxy)benzoic acid;
2-[[6-(2-hydroxyphenoxy)hexyl]oxy]-3-(tetradecyloxy)benzoic acid;
2-[[6-(2,3-dihydroxyphenyl)hexyl]oxy]-3-(octadecyloxy)benzoic acid;
2-[3-(2,3-dihydroxyphenyl)propoxy]-3-(octadecyloxy)benzoic acid;
2-[[6-(2,3-dihydroxyphenyl)hexyl]oxy]-3-(tetradecyloxy)benzoic acid;
2-[[6-(2,3-dihydroxyphenyl)hexyl]oxy]-3-(decyloxy)benzoic acid;
3-[[6-(2,3-dihydroxyphenyl)hexyl]oxy]-5-(dodecyloxy)benzoic acid;
3-[[6-(2,3-dihydroxyphenyl)hexyl]oxy]-5-(hexadecyloxy)benzoic acid;
3-[3-(2,3-dihydroxyphenyl)propoxy]-5-(octadecyloxy)benzoic acid;
3-[4-(2,3-dihydroxyphenyl)butoxy]-5-(octadecyloxy)benzoic acid;
3-[[5-(2,3-dihydroxyphenyl)pent]oxy]-5-(octadecyloxy)benzoic acid;
3-[[8-(2,3-dihydroxyphenyl)octyl]oxy]-5-(hexadecyloxy)benzoic acid;
3-[[6-(3,4-dihydroxyphenyl)hexyl]oxy]-5-(octadecyloxy)benzoic acid;
3-[[6-(3,4-dihydroxyphenyl)hexyl]oxy]-5-(decyloxy)benzoic acid;
3-[[6-(3,4-dihydroxyphenyl)hexyl]oxy]-5-(tetradecyloxy)benzoic acid;
3-(tetradecyloxy)-5-(2,2-diphenyl-1-oxoethoxy)benzoic acid;
3-(decyloxy)-5-(2,2-diphenyl-1-oxoethoxy)benzoic acid;
3-(tetradecyloxy)-5-[(tricyclo[3.3.1./3,7/]dec-1-ylcarbonyl)oxy]benzoic acid, and
3-(decyloxy)-5-[(tricyclo[3.3.1./3,7/]dec-1-ylcarbonyl)oxy]benzoic acid.

The compounds of formula I can be prepared as set forth in Schemes 1–3.

SCHEME 1

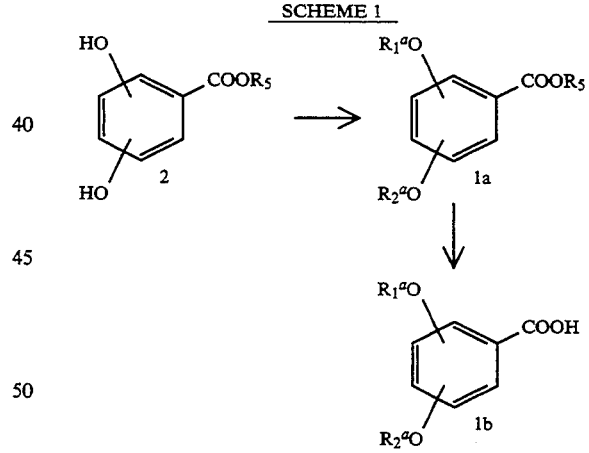

wherein $R_1{}^a$ and $R_2{}^a$ are the same, and are
$R_4(CH_2)_p-$
$R_4$, and p are as defined
$R_5$ is lower alkyl or benzyl In Scheme 1, a known compound of formula 2 can be converted to the corresponding dialkylated compound of formula 1a by treatment with an excess of the corresponding alkyl halide in the presence of a base, such as an alkali metal carbonate, in a solvent, such as acetone, DMF or mixtures thereof, at a temperature in the range of from 56° to 100°. The resultant ester of formula 1a can be converted to the corresponding acid of formula 1b by base hydrolysis using an alkali metal hydroxide in a solvent, such as methanol with added dioxane, if needed to improve solubility, at temperatures in the range of from 25° to 65°. Compounds of formula 1a, wherein $R_5$ is benzyl, can also be converted to compounds of formula 1b by catalytic hydrogenolysis under standard conditions, such as shaking under a hydrogen atmosphere, in a solvent, such as THF or ethyl acetate, in the presence of a catalyst, such as palladium.

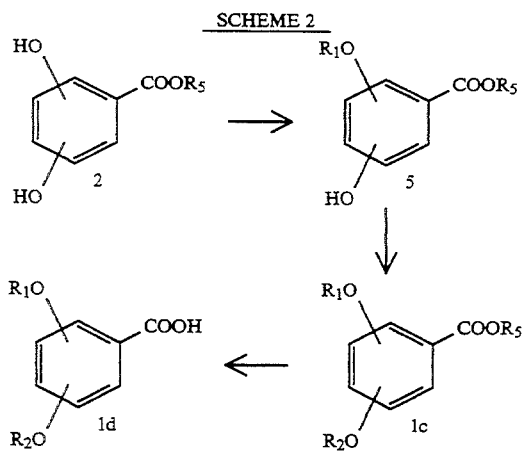

SCHEME 2 wherein $R_1$ and $R_2$ are not the same and are as previously described and $R_5$ is also as previously described.

In Scheme 2, a known compound of formula 2 can be converted to the corresponding monoalkylated compound of formula 5 by treatment with an equimolar quantity of the corresponding alkyl halide in the presence of a base, such as an alkali metal carbonate, in a solvent, such as acetone, DMF or mixtures thereof, at a temperature in the range of from 56° to 100°. The resultant compound of formula 5 can be converted to the corresponding compound of formula 1c by treatment with a different alkyl halide utilizing the same reaction conditions. Treatment of a compound of formula 5 with 1-adamantanecarboxylic acid chloride or diphenylacetyl chloride provides the corresponding compounds of formula 1c. wherein $R_2$ is 1-adamantyl—CO— or diphenylmethyl—CO—. Finally, base hydrolysis of 1c using an alkali metal hydroxide in a solvent, such as methanol with added dioxane, if needed to improve solubility, at temperatures in the range of from 25° to 65°. Compounds of formula 1c, wherein $R_5$ is benzyl, can also be converted to compounds of formula 1d by catalytic hydrogenolysis under standard conditions, such as shaking under a hydrogen atmosphere, in a solvent, such as THF or ethyl acetate, in the presence of a catalyst, such as palladium. When $R_2$ is 1-adamantyl—CO— or diphenylmethyl—CO— and $R_5$ is benzyl in 1c, catalytic hydrogenolysis must be used to convert 1c to 1d.

Alternatively, the $R_2$ group could be added first followed by the $R_1$ group.

The acids of formulas 1b and 1d can be converted to the corresponding prodrug esters 1, R is —$(CH_2)_2N(R_3)_2$ or —$CH_2OOCR_3$, using known procedures. For example, treatment of 1d with a dilower alkylaminoethyl chloride (such as diethylaminoethyl chloride) or a chloromethyl lower alkanoate (such as chloromethyl acetate), in the presence of a tertiary amine, such as triethyl amine or N,N-diisopropylethylamine, in a solvent such as acetone or DMF at a temperature in the range from 25° to 80° gives the corresponding esters 1, R is —$(CH_2)_2N(R_3)_2$ or —$CH_2OOCR_3$ respectively.

In addition, the acids 1b and 1d can be converted to the esters 1a and 1c where $R_5$ is lower alkyl by treatment with the corresponding lower alkyl halide, preferably the iodide, in the presence of an alkali metal bicarbonate in a solvent, such as, DMF at temperatures in the range of from 25° to 100°.

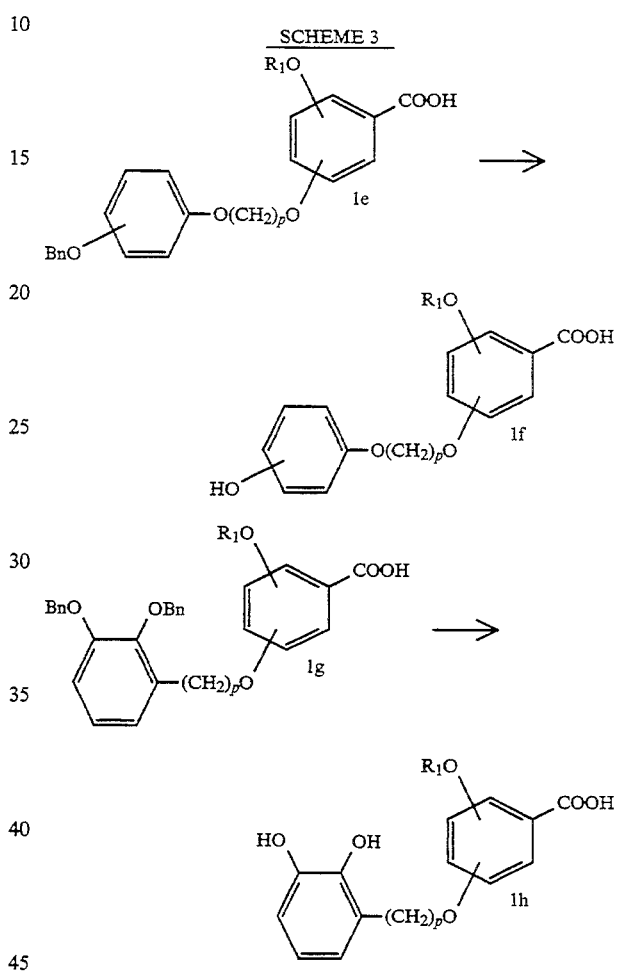

SCHEME 3

$R_1$ and p are as defined and Bn is benzyl

If $R_1$ or $R_2$ in 1d contain a benzyloxy substituent, such compounds (1e or 1g) can be converted to the corresponding hydroxy derivatives 1f and 1h, respectively according to Scheme 3. This can be accomplished by catalytic hydrogenolysis under the standard conditions described above.

The invention also relates to salts of the compounds of formula 1 when they contain an acidic functionality, such as when R is hydrogen, which lends itself to salt formation with a base. Salts of the compounds of formula 1 which have a carboxy group are prepared by the reaction with a base having a non-toxic, pharmacologically acceptable cation. In general, any base which will form a salt with a carboxylic acid and whose pharmacological properties will not cause an adverse physiological effect is within the scope of this invention.

Suitable bases thus include, for example, the alkali metal and alkaline earth metal hydroxides, carbonates or the like, for example, calcium hydroxide, sodium hydroxide, sodium carbonate, potassium carbonate or the like, ammonia, primary, secondary and tertiary amines, such as monoalkylamines, dialkylamines, trialkylamines, for example, methylamine, diethylamine, triethylamine or the like, nitrogen containing heterocyclic amines, for example, piperidine or the like. A salt thus produced is the functional equivalent of the corresponding compound of formula 1 wherein R is hydrogen and one skilled in the art will appreciate that the variety of salts embraced by the invention is limited only by the criterion that a base employed in forming the corresponding salts be both non-toxic and physiologically acceptable.

The useful activity of the compounds of formula 1 as phospholipase $A_2$ ($PLA_2$) inhibitors can be demonstrated as hereinafter set forth.

The compounds of formula 1 are potent inhibitors of phospholipases $A_2$($PLA_2$'s) and are therefore useful in the treatment of diseases, such as psoriasis, inflammatory bowel disease, asthma, allergy, arthritis, dermatitis, gout, pulmonary disease, myocardial ischemia, and trauma induced inflammation, such as spinal cord injury.

Assay for Inhibition of HSF-$PLA_2$ In Vitro

The $PLA_2$ used in this test is the extracellular enzyme obtained from human synovial fluid (HSF-$PLA_2$).

The assay for HSF-$PLA_2$ activity was a modification of the described method [Franson R., Dobrow R., Weiss, J., Elsbach P., and Weglick W. B., J. Lipid Res., 19, 18–23 (1978)] which was conducted using [1-$^{14}$C]-oleate-labelled $E.$ $coli$ substrate in excess at a final concentration of 20,000 dpm/ml. This was equivalent to 18.2 mM of cell membrane phospholipid phosphorus and $2 \times 10^9$ autoclaved $E.$ $coli$/ml. The optimal conditions which were developed for the assay of HSF-$PLA_2$ inhibitors are summarized as follows. A total volume of 0.5 ml of reaction mixture typically had the following final composition: substrate (20,000 dpm/ml); enzyme (0.1% HSF, v/v); 2 mM $CaCl_2$; 150 mM $Na^+$; 50 mM sodium HEPES buffer, pH 7.3; and 1% dimethyl sulfoxide (DMSO, used to solubilize test inhibitors) in the presence or absence of inhibitor. The reaction was initiated by the addition of HSF-$PLA_2$ and duplicate samples of the mixture were incubated in $13 \times 100$ mm glass tubes with shaking for 30 minutes at $37°$ C. The reaction was terminated by the addition of 2.5 ml of chloroform-methanol (1 to 1.5, v/v). The extraction of lipids from the stopped reaction mixture was conducted by the further additions of 0.5 ml of chloroform and 1 ml of water with mixing. After centrifuging, the lower chloroform phase was transferred to smaller glass tubes and the solvent was evaporated to dryness with a nitrogen stream. The extracted lipid residue was redissolved in 50 ml of a solution containing carrier oleic acid (0.2 mg/ml) of chloroformmethanol [9 to 1, v/v]). The whole lipid extract was applied to a preactivated (30 minutes at $110°$ C.) silica gel-impregnated glass fiber thin layer chromatography sheet (ITLC type SG sheet from Gelman Sciences Inc., Ann Arbor, Mich.) using hexane-acetic acid (100 to 1, v/v) as the developing solvent. This TLC system rapidly (6 minutes) resolved the enzymatically released product, $^{14}$C-oleic acid, from the unreacted $^{14}$C-phospholipid substrate. The unsaturated lipids were located on the chromatogram by a brief exposure to iodine vapor. The oleic acid zone ($R_f$ value 0.95) and phospholipid zone (origin) were cut out, chopped into small pieces, shaken with 2 ml of ethanol-water (80 to 20, v/v) and 15 ml of Aquasol and counted for radioactivity. A control incubation of substrate in the absence of HSF-$PLA_2$ was performed in each experiment. The $PLA_2$ activity of the human synovial fluid was corrected for this small control value. In the absence of inhibitors, these optimal conditions resulted in approximately 18% hydrolysis of substrate (corrected for a substrate blank of <2%). The specific activity of $PLA_2$ in the pooled human synovial fluid under the optimal assay conditions was 49.2 nmoles [1-$^{14}$C]-oleic acid released hour$^{-1}$ mg$^{-1}$. The $IC_{50}$ ($\mu$M concentration of test compound that produces 50% inhibition of $PLA_2$ activity) was determined for each test compound. The results are reported in Tables I and II.

Croton Oil Mouse Ear Edema Test

The croton oil-induced mouse ear edema test, a model of irritant-induced contact dermatitis, has been used for evaluation of the $PLA_2$ inhibitors by the topical route of administration. This test was carried out as described in the following references:

Weirich, E. G., Longauer, J. K and Kirkwood, A. A. Arch Dermatol. Res. 259: 141–149, 1977.

Tubaro, A., Dri, P., Delbello, G., Zilli, C. and Della Loggia, R. Agents and Actions, 17: 347–349, 1985.

The major active ingredient in croton oil is the tumor promoter 12-O-tetradecanoylphorbol-13-acetate (TPA) and the topical application of TPA to mouse skin has been reported to cause an increase in epidermal $PGE_2$ production as well as an increase in epidermal cell membrane $PLA_2$ activity. Indomethacin, an inhibitor of prostaglandin synthesis, prevented the TPA-mediated increase in epidermal $PGE_2$ levels as well as the TPA-mediated induction of epidermal cell ornithine decarboxylase. Furthermore, the application of $PGE_2$ to mouse skin countered the inhibitory effect of indomethacin upon TPA-stimulated cellular proliferation. Taken together these data suggest that the croton oil mouse ear edema test is a valid model for the topical evaluation of $PLA_2$ inhibitors.

Twenty five $\mu$l of a 1% croton oil solution [dissolved in a mixture of pyridine/water/diethyl ether at a ratio of 5/20/75 (croton oil vehicle)] are applied to the outer side of the right ear of 3–4 week old male CD-1 mice (8 animals per group). The test compounds are dissolved directly in the 1% croton oil solution at various concentrations and coapplied. Control animals receive 25 $\mu$l of croton oil vehicle on the right ear. Biopsy punches are removed at 6 hours from the fight ear of the animals using a 6 mm skin trephine (Roboz, Washington, D.C.) and the wet weight of the ear punches is determined. The weight of the biopsy punches is a measure of ear inflammation, primarily edema. The data are expressed as percent inhibition relative to control groups.

The in vivo activity of representative compounds of formula 1 in the croton oil ear edema test are reported in Table I.

Statistical analysis of the mean edema values of the control versus the treated groups is performed using Student's t-test. The significance of changes from the mean value for vehicle-treated (control) animals in the following Tables is indicated as follows: *p<0.05, p<0.01, *p<0.005, ns/not significant.

TABLE I

| Ex No | Name | % Inhib of HSF-PLA$_2$ | % Inhib of Croton Oil Mouse Ear Edema (1 mg) |
|---|---|---|---|
| 6 | 3,5-bis[3-(1,1'-biphenyl-4-yloxy)propoxy]benzoic acid | 50 (3 μM) | NT |
| 8A | 3,5-bis[2-(1-naphthalenyloxy)ethoxy]benzoic acid | 67 (10 μM) | NT |
| 11 | 3-(octadecyloxy)-5-(2,2-diphenyl-1-oxoethoxy)benzoic acid | 50 (0.3 μM) | 71*** |
| 13 | 3-(octadecyloxy)-5-[(tricyclo[3.3.1./3,7/]dec-1-ylcarbonyl)oxy]benzoic acid | 86 (5 μM) | 81*** |
| 15 | 3-[2-(2-naphthalenyloxy)ethoxy]-5-(octadecyloxy)benzoic acid | 77 (10 μM) | NT |
| 17 | 3-(octadecyloxy)-5-(3-phenoxypropoxy)benzoic acid | 50 (1.4 μM) | 81*** |
| 19 | 3-[[6-(2,3-dihydroxyphenyl)hexyl]oxy]-5-(octadecyloxy)benzoic acid | 50 (1.1 μM) | 76*** |
| 30 | 3-[[3-(4-phenylmethoxy)phenoxy]propoxy]-5-(octadecyloxy)benzoic acid | NT | 62*** |
| 31 | 3-[3-(4-hydroxyphenoxy)propoxy]-5-(octadecyloxy)benzoic acid | 37 (1 μM) | 84*** |

TPA Induced Mouse Ear Edema Test

The TPA-induced mouse ear edema test, a model of irritant-induced contact dermatitis is described in the following reference: J. M. Young, B. M. Wagner and D. A. Spires, J. Invest. Dermatology 80, 48–52 (1983).

For this test, 10 μl of 12-O-tetradecanoylphorbol-13-acetate (TPA), dissolved in a vehicle of pyridine: water: diethyl ether (20:5:75), was applied to the outside of the right ear of 3–4 week old male CD-1 mice (8 animals per group). The test compounds were dissolved in the same vehicle and 10 μl was applied to the inside of the same ear 30 minutes prior to the application of TPA. Ear punches (6 mm) were removed at 6 hours after TPA application, weighed and assayed for myeloperoxidase (MPO) activity as described in the following reference: P. P. Bradley, D. A. Priebat, R. D. Christensen and G. Rothstein, J. Invest. Dermatology 78, 206–209 (1982). The wet weight of the ear biopsy punches is a measure of the ear edema and the level of MPO activity in the ear punches is an indicator of neutrophil infiltration. The data are expressed as percent inhibition of drug-treated animals relative to the control group.

The in vivo activity of representative compounds of formula 1 in the TPA mouse ear edema test is reported in Table II.

TABLE II

| Ex No | Name | % Inhib of HSF-PLA$_2$ | % Inhib of TPA Mouse Ear Edema (1 mg) |
|---|---|---|---|
| 19 | 3-[[6-(2,3-dihydroxyphenyl)hexyl]oxy]-5-(octadecyloxy)benzoic acid | 50 (1.1 μM) | 55*** (0.3 mg) |
| 24 | 3-[3-[4-(methylsulfinyl)phenoxy]propoxy]-5-(octadecyloxy)benzoic acid | 72 (10 μM) | 43*** |
| 26 | 3-[3-[4-(methylsulfonyl)phenoxy]propoxy]-5-(octadecyloxy)benzoic acid | 86 (10 μM) | 42*** |
| 31 | 3-[3-(4-hydroxyphenoxy)propoxy]-5-(octadecyloxy)benzoic acid | 37 (1 μM) | 58*** (0.3 mg) |
| 34 | 3-[3-(4-hydroxyphenoxy)propoxy]-5-(octadecyloxy)benzoic acid methyl ester | 2 (10 μM) | 42*** |
| 36 | 3-[3-[4-(phenylmethoxy)phenoxy]propoxy]-5-(tetradecyloxy)benzoic acid | 87 (10 μM) | 52** |
| 37 | 3-[3-(4-hydroxyphenoxy)propoxy]-5-(tetradecyloxy)benzoic acid | 75 (10 μM) | 57** |
| 39 | 3-(decyloxy)-5-[3-[4-(phenylmethoxy)phenoxy]propoxy]benzoic acid | 61 (10 μM) | NT |
| 40 | 3-(decyloxy)-5-[3-(4-hydroxyphenoxy)propoxy]benzoic acid | 50 (8.8 μM) | 58*** (0.3 mg) |
| 41 | 3,5-bis[3-[4-(phenylmethoxy)phenoxy]propoxy]benzoic acid | 54 (10 μM) | 54** |
| 42 | 3,5-bis[3-(4-hydroxyphenoxy)propoxy]benzoic acid | 5 (10 μM) | 43** |
| 44 | 3-[[6-(4-hydroxyphenoxy)hexyl]oxy]-5-(octadecyloxy)benzoic acid | 94 (10 μM) | 46** |
| 46 | 3-[3-(2-hydroxyphenoxy)propoxy]-5-(octadecyloxy)benzoic acid | 91 (10 μM) | 47*** (0.3 mg) |
| 49 | 5-(octadecyloxy)-2-[3-[4-(phenylmethoxy)phenoxy]propoxy]benzoic acid | 79 (10 μM) | 27** (0.3 mg) |
| 50 | 2-[3-(4-hydroxyphenoxy)propoxy]-5-(octadecyloxy)benzoic acid | 93 (10 μM) | 45** |
| 53 | 4-(octadecyloxy)-2-[3-[4-(phenylmethoxy)phenoxy]propoxy]benzoic acid | 55 (10 μM) | 17 ns |
| 54 | 2-[3-(4-hydroxyphenoxy)propoxy]-4-(octadecyloxy)benzoic acid | 79 (10 μM) | 31* |

TABLE II-continued

| Ex No | Name | % Inhib of HSF-PLA$_2$ | % Inhib of TPA Mouse Ear Edema (1 mg) |
|---|---|---|---|
| 57 | 3-(octadecyloxy)-2-[3-[4-(phenylmethoxy)phenoxy]propoxy]benzoic acid | 91 (10 μM) | 62*** |
| 58 | 2-[3-(4-hydroxyphenoxy)propoxy]-3-(octadecyloxy)benzoic acid | 93 (10 μM) | 48*** (0.3 mg) |
| 61 | 3-[[6-(2,3-dihydroxyphenyl)hexyl]oxy]-5-(tetradecyloxy)benzoic acid methyl ester | 17 (10 μM) | 44*** |
| 63 | 3-[[6-(2,3-dihydroxyphenyl)hexyl]oxy]-5-(tetradecyloxy)benzoic acid | 88 (10 μM) | 61*** (0.3 mg) |
| 66 | 3-(decyloxy)-5-[[6-(2,3-dihydroxyphenyl)hexyl]oxy]benzoic acid methyl ester | 22 (10 μM) (0.3 mg) | 55*** |
| 68 | 3-(decyloxy)-5-[[6-(2,3-dihydroxyphenyl)hexyl]oxy]benzoic acid | 74 (20 μM) (0.3 mg) | 58*** |
| 71 | 3-(decyloxy)-5-[[6-(2,3-dihydroxyphenyl)hexyl]oxy]benzoic acid 2-(diethylamino)ethyl ester monohydrochloride salt | NT | 57** |
| 72 | 3-(decyloxy)-5-[[6-(2,3-dihydroxyphenyl)hexyl]oxy]benzoic acid (acetyloxy) methyl ester | NT | 52*** (0.1 mg) |

The following representative compounds of the invention inhibited myeloperoxidase in the TPA mouse ear test when tested at 0.3 mg topically:

| Ex. No. | Name | % Inhib |
|---|---|---|
| 19 | 3-[[6-(2,3-dihydroxyphenyl)hexyl]oxy]-5-(octadecyloxy)benzoic acid | 94 |
| 31 | 3-[3-(4-hydroxyphenoxy)propoxy]-5-(octadecyloxy)benzoic acid | 70 |
| 40 | 3-(decyloxy)-5-[3-(4-hydroxyphenoxy)propoxy]benzoic acid | 72 |
| 58 | 2-[3-(4-hydroxyphenoxy)propoxy]3-(octadecyloxy)benzoic acid | 62 |
| 63 | 3-[[6-(2,3-dihydroxyphenyl)hexyl]oxy]-5-(tetradecyloxy)benzoic acid | 61 |
| 68 | 3-(decyloxy)-5-[[6-(2,3-dihydroxyphenyl)hexyl]oxy]benzoic acid | 89 |

Phospholipase A$_2$ Rat Paw Edema

Representative compounds of the invention were tested in rats to determine their ability to inhibit the acute inflammatory response induced by the injection of snake venom phospholipase A$_2$. Test compounds were administered intraperitoneally or orally to groups of seven Lewis rats (~200 gm) 1 hr prior to phospholipase A$_2$ administration. The test compounds were dissolved in dimethyl sulfoxide for intraperitoneal administration and dissolved or suspended in Labrafil M-1944CS for oral administration. At 0 hr, 5 μg (10 units) of purified phospholipase A$_2$ from Naja naja venom (Sigma Chem. Co.) dissolved in 0.1 mL of pyrogen free saline was injected subplantarly into the right hind paw to elicit the inflammatory response. The volume (in mL) of the right hind paw was measured by immersion of the paw to the level of the lateral malleolus in an aqueous plethysmometer immediately prior to the injection of phospholipase A$_2$ and then at 0.5, 2 and 4 hr after phospholipase A$_2$ injection. The paw edema was calculated by subtracting the zero time reading from the readings taken after injection. The percent change of the edema volume from the vehicle treated control was calculated to determine the activity of the test compound.

An exemplary compound of the invention was tested: 3-(octadecyloxy)-5-(2,2-diphenyl-1-oxoethoxy)benzoic acid gave 29%* inhibition of edema measured 2 hours after PLA$_2$ injection when tested at 30 mg/kg ip.

Rat Carrageenan Paw Edema

Representative compounds of the invention were tested in the rat carrageenan-induced paw edema test to determine their ability to inhibit this acute inflammatory response. Test compounds were administered intraperitoneally or orally to groups of seven Lewis rats (~200 gm) 1 hr prior to carrageenan administration. The test compounds were dissolved in dimethyl sulfoxide for intraperitoneal administration and dissolved or suspended in Labrafil M-19944CS for oral administration. At 0 hour, 0.1 mL of 1% carrageenan dissolved in pyrogen free saline was injected subplantarly into the right hind paw to elicit the inflammatory response. The volume (in mL) of the right hind paw was measured by immersion of the paw to the level of the lateral malleolus in an aqueous plethysmometer immediately prior to the injection of carrageenan and then at 1, 2 and 4 hr after carrageenan injection. The paw edema was calculated by subtracting the zero time reading from the readings taken after injection. The percent change of the edema volume from the vehicle treated control was calculated to determine the activity of the test compound. Statistical analysis of the mean paw edema values of the control versus the treated groups was performed using Student's t-test.

3-[3-(4-hydroxyphenoxy)propoxy]-5-(octadecyloxy)-benzoic acid, was tested at 30 mg/kg ip and gave 55%* inhibition of the edema measured at 2 hours after carrageenan injection.

Acetic Acid-Induced Colitis in Rats

The rat acetic acid-induced colitis bioassay has been described by J. E. Krawisz, et al. in Amer. J. Proc. Gastro. Col. Rec. Surg. 31:11–18 (1980), and by P. Sharon and W. F. Stenson in Gastroenterology 88, 55–63 (1985) and 86, 453–460 (1984). Acetic acid-induced colitis is characterized by the movement of inflammatory cells into the colon, with the number of such cells in the mucosa being measured by the activity of myeloperoxidase, a marker enzyme for these cells. Positive desirable activity is indicated by a reduction in the high levels of myeloperoxidase caused by acetic acid. Male rats (Sprague-Dawley), weighing 150 to 300 g, were pretreated twice daily for two days with either the vehicle (water or dimethylsulfoxide) or the test inhibitor compound suspended in water or dissolved in dimethylsulfoxide and orally administered. On the third day, the animals were dosed the same as on the previous two days, anesthetized with metofane, and 2 ml of 2.5% acetic acid was injected by syringe into the colonic lumen, followed immediately by 3 ml of air and a rinse consisting of 3 ml of phosphate-buffered saline (the acetic acid is present in the lumen for a sufficient period to cause inflammation without producing severe necrosis or irreversible damage). The animals were administered a second dose of the test compound in the same amount about 16 hours later. Then 24 hours after the acetic acid treatment, the animals were sacrificed. The colonic mucosa was surgically removed and homogenized in an aqueous buffer at pH 6 with a Tissumizer or similar device and myeloperoxidase was measured in the homogenate using o-phenylenediamine as a chromagen, as described by A. Voller, D. E. Bidwell and A. Bartlett in "The Enzyme Linked Immunosorbent Assay (ELISA)", Zoological Soc., London, 1979, pages 29–30. Control animals were pretreated with the vehicle and saline in place of acetic acid.

Data for a representative compound of the invention is reported below:

3-[[6-(2,3-Dihydroxyphenyl)hexyl]oxy]-5-(octadecyloxy)benzoic acid gave 56±17% inhibition of myeloperoxidase at a dose of 10 mg/kg orally.

In practice of the invention, the dose of a compound of formula 1 or a salt thereof to be administered and the frequency of administration will be dependent on the potency and duration of activity of the particular compound of formula 1 or salt to be administered and on the route of administration, as well as the severity and nature of the condition and age of the mammal to be treated and the like. Oral doses of a compound of formula 1 or a salt thereof contemplated for use in practicing the invention can be in the range of from 10 mg to about 2.0 g per day, preferably about 50 mg to about 1 g per day, either as a single dose or in divided doses. For topical use a compound of formula I or salt thereof contemplated for use in practicing the invention is present in the topical composition in the range of from about 1 to about 10%, preferably from about 2 to about 5%.

A compound of formula 1, or a salt or a composition containing a therapeutically effective amount of a compound of formula 1, or a salt thereof can be administered by methods well known in the art. Thus, a compound of formula 1, or a salt thereof can be administered either singly or with other pharmaceutical agents, for example, antihistamines, mediator release inhibitors, methyl xanthines, beta agonists or antiasthmatic steroids such as prednisone and prednisolone, orally, parenterally, rectally, or by inhalation, for example in the form of an aerosol, micropulverized powder or nebulized solution. For oral administration, they can be administered in the form of tablets, capsules, for example, in admixture with talc, starch, milk sugar or other inert ingredients, that is, pharmaceutically acceptable carriers, or in the form of aqueous solutions, suspensions, elixirs or aqueous alcoholic solutions, for example, in admixture with sugar or other sweetening agents, flavoring agents, colorants, thickeners and other conventional pharmaceutical excipients. For parenteral administration, they can be administered as solutions or suspension, for example, as an aqueous or peanut oil suspension using excipients and carriers conventional for this mode of administration. For administration as aerosols, they can be dissolved in a suitable pharmaceutically acceptable solvent, for example, ethyl alcohol or combinations of miscible solvents, and mixed with a pharmaceutically acceptable propellant. Such aerosol compositions are packaged for use in pressurized container fitted with an aerosol valve suitable for release of the pressurized composition. Preferably, the aerosol valve is a metered valve, that is one which on activation releases a predetermined effective dose of the aerosol composition. For topical use, they can conveniently be used in the form of salves, tinctures, creams, solutions, lotions, sprays, suspensions and the like. Salves and creams as well as solutions are preferred. These topical preparations can be prepared by mixing a compound of formula I as an active ingredient with one or more non-toxic, inert, solid or liquid carriers which are usual in such preparations and which are suitable for topical treatment.

EXPERIMENTAL SECTION

The Examples which follow further illustrate the invention. All temperatures set forth in the specification and the Examples are in degrees Centigrade. Melting points were taken on a Thomas Hoover capillary melting point apparatus and are uncorrected. All compounds were characterized by proton magnetic resonance spectra taken on a Varian XL-200 or XL-400 spectrometer and electron impact or fast atom bombardment mass spectra taken on either VG ZAB-1F or VG 70E-HF mass spectrometers. Preparative high-pressure liquid chromatography (HPLC) was performed on silica gel Prep-Pak 500 cartridges using a Waters Associates Prep LC 500A. Extracts were dried over anhydrous magnesium sulfate unless otherwise noted.

EXAMPLE 1

3,5-bis(3-Phenylpropoxy)benzoic acid methyl ester

A mixture of 1.68 g (0.01 mol) of 3,5-dihydroxybenzoic acid methyl ester, 3.4 mL (0.022 mol) of 3-bromopropylbenzene and 2.8 g (0.02 mol) of potassium carbonate in 50 mL of anhydrous DMF was stirred and heated at 100° for 18 hours. The solvent was removed at reduced pressure, the residue was acidified and the product was extracted with ethyl acetate. The dried extract was concentrated to dryness and the residue was purified by chromatography on 150 g of silica gel using 10 % ethyl acetate-hexane to give 3.0 g of 3,5-bis(3-phenylpropoxy)benzoic acid methyl ester as an oil. The nmr and mass spectra were consistent with the structure.

EXAMPLE 2

3,5-bis(3-Phenylpropoxy)benzoic acid

A solution of 3.0 g (7.4 mmol) of 3,5-bis(3-phenylpropoxy)benzoic acid methyl ester and 15 mL (15 mmol) of 1N NaOH in 100 mL of methanol and 40 mL of dioxane was stirred at reflux for 16 hours. The solvents were removed at reduced pressure, the residue was acidified and the product was extracted with ethyl acetate. The dried extract was concentrated to an oil which was crystallized from methanol-water to give 2.56 g, mp 107°–109° of 3,5-bis(3-phenyl-propoxy)benzoic acid.

Anal. Calcd for $C_{25}H_{26}O_4$: C, 76.90; H, 6.71. Found: C, 76.42; H, 6.77.

EXAMPLE 3

4-(3-Bromopropoxy)-1,1-biphenyl

A mixture of 6 g (0.035 mol) of 4-phenylphenol, 11 mL (0.11 mol) of 1,3-dibromopropane and 7.5 g (0.054 mol) of potassium carbonate in 100 mL of acetone was stirred at reflux for 18 hours. The solvent was removed at reduced pressure and the residue was extracted with ethyl acetate. The extract was concentrated to a solid which was purified by HPLC using 10% ether-hexane to give 5.5 g, mp 60°–63°, of 4-(3-bromopropoxy)-1,1-biphenyl. The structure was confirmed by nmr and mass spectra.

EXAMPLE 4

3,5-bis[3-(1,1'-Biphenyl-4-yloxy)propoxy]benzoic acid methyl ester

A mixture of 0.79 g (4.7 mmol) of 3,5-dihydroxybenzoic acid methyl ester, 3.0 g (10.3 mmol) of 4-(3-bromopropoxy)-1,1-biphenyl, 1.55 g (10.3 mmol) of sodium iodide and 3.9 g (28 mmol) of potassium carbonate in 80 mL of anhydrous acetone and 40 mL of DMF was stirred at reflux for 39 hours. The solvents were removed at reduced pressure, water was added to the residue and the product was extracted with chloroform. The dried extract was concentrated to a solid which was purified by chromatography on 90 g of silica gel using chloroform to give 1.5 g (54% yield, mp 142°–145°) of 3,5-bis [3-(1,1'-biphenyl-4-yloxy)propoxy]benzoic acid methyl ester.

Anal. Calcd for $C_{38}H_{36}O_6$: C, 77.53; H, 6.16. Found: C. 77.48; H, 5.83.

EXAMPLE 5 A

Using this procedure, the reaction of 3,5-dihydroxybenzoic acid methyl ester with 2-(3-bromopropoxy)-1,1-biphenyl gave 3,5-bis[3-(1,1'-biphenyl-2-yloxy)propoxy]benzoic acid methyl ester, mp 77°–79°. Anal. Calcd for $C_{38}H_{36}O_6$: C, 77.53; H, 6.16. Found: C, 77.31; H, 6.15.

EXAMPLE 5 B

Using this procedure, the reaction of 3,5-dihydroxybenzoic acid methyl ester with 3-(3-bromopropoxy)-1,1-biphenyl gave 3,5-bis[3-(1,1'-biphenyl-3-yloxy)propoxy]benzoic acid methyl ester as an oil. The structure was confirmed by nmr and mass spectra.

EXAMPLE 6

3,5-bis[3-(1,1'-Biphenyl-4-yloxy)propoxy]benzoic acid

A solution of 1.5 g (2.55 mmol) of 3,5-bis[3-(1,1'-biphenyl-4-yloxy)propoxy]benzoic acid methyl ester and 15 mL (15 mmol) of 1N NaOH in 45 mL of methanol and 40 mL of dioxane was stirred at reflux for 6 hours. The reaction mixture was concentrated at reduced pressure, the residue was acidified and the product was filtered and recrystallized from ethyl acetate to give 1.3 g (89% yield, mp 186°–187°) of 3,5-bis[3-(1,1'-biphenyl-4-yloxy)propoxy]benzoic acid.

Anal. Calcd for $C_{37}H_{34}O_6$: C, 77.33; H, 5.96. Found: C, 77.28; H, 5.90.

EXAMPLE 6 A

Using this procedure, base hydrolysis of 3,5-bis[3-(1,1'-biphenyl-2-yloxy)propoxy]benzoic acid methyl ester gave 3,5-bis[3-(1,1'-biphenyl-2-yloxy)propoxy]benzoic acid, mp 110°–113°. The nmr and mass spectra were consistent with the structure.

EXAMPLE 6 B

Using this procedure, base hydrolysis of 3,5-bis[3-(1,1'-biphenyl-3-yloxy)propoxy]benzoic acid methyl ester gave 3,5-bis[3-(1,1'-biphenyl-3-yloxy)propoxy]benzoic acid, mp 65°–69°. The nmr and mass spectra were consistent with the structure.

EXAMPLE 7

3,5-bis[2-[2-(Naphthalenyloxy)ethoxy]benzoic acid methyl ester

A mixture of 0.90 g (5.3 mmol) of 3,5-dihydroxybenzoic acid methyl ester, 2.95 g (11.8 mmol) of 2-(2-bromoethoxy)naphthalene, 1.8 g (11.8 mmol) of sodium iodide and 3 g (21.7 mmol) of potassium carbonate in 80 mL of acetone and 25 mL of DMF was stirred at reflux for 40 hours. The solvents were removed at reduced pressure, water was added to the residue and the product was extracted with ethyl acetate. The dried extract was concentrated to a solid which was recrystallized from ethyl acetate to give 1.6 g (59% yield, mp 132°–137°) of 3,5-bis[2-[2-(naphthalenyloxy) ethoxy]benzoic acid methyl ester.

Anal. Calcd for $C_{32}H_{28}O_6$: C, 75.58; H, 5.55. Found: C, 75.19; H, 5.44.

EXAMPLE 7 A

Using this procedure, reaction of 3,5-dihydroxybenzoic acid methyl ester with 1-(2-bromoethoxy)naphthalene gave 3,5-bis[2-(1-naphthalenyloxy)ethoxy]benzoic acid methyl ester, mp 132°–137°, Anal. Calcd for $C_{32}H_{28}O_6$: C, 75.58; H, 5.55. Found: C, 75.19: H, 5.44.

EXAMPLE 8

3,5-bis[2-[2-(Naphthalenyloxy)ethoxy]benzoic acid

A solution of 1.6 g (3.15 mmol) of 3,5-bis[2-[2-(naphthalenyloxy) ethoxy]benzoic acid methyl ester and 15 mL (15 mmol) of 1N NaOH in 45 mL of methanol and 20 mL of dioxane was stirred at reflux for 2 hours. The usual workup followed by recrystallization from THF-ethyl acetate gave 1.2 g (77% yield, mp 205°–207°) of 3,5-bis[2-[2-(naphthalenyloxy)ethoxy]benzoic acid.

Anal. Calcd for $C_{31}H_{26}O_6$: C, 75.29; H, 5.30. Found: C, 74.60; H, 5.26.

EXAMPLE 8 A

Using this procedure, base hydrolysis of 3,5-bis[2-(1-naphthalenyloxy)ethoxy]benzoic acid methyl ester gave 3,5-bis[2-(1-naphthalenyloxy)ethoxy]benzoic acid, mp 213°–215°. Anal. Calcd for $C_{31}H_{26}O_6$: C, 74.29; H, 5.30. Found: C, 74.58; H, 5.36.

EXAMPLE 9

3-Hydroxy-5-(octadecyloxy)benzoic acid phenylmethyl ester

A mixture of 30 g (0.123 mol) of 3,5-dihydroxybenzoic acid phenylmethyl ester, 40.9 g (0.123 mol) of 1-bromooctadecane, 17 g (0.123 mol) of anhydrous potassium carbonate in 500 ml of acetone and 10 ml of DMF was stirred at reflux for 25 hours. The reaction mixture was filtered and the filtrate was concentrated at reduced pressure to a solid. The residue was treated with water and the product was extracted with methylene chloride. The dried extract was concentrated at reduced pressure to a solid which was purified by HPLC using 1% ethyl acetate-methylene chloride to give 22 g (36% yield, mp 72°–75°) of 3-hydroxy-5-(octadecyloxy)benzoic acid phenylmethyl ester. The structure was confirmed by nmr and mass spectra.

EXAMPLE 10

3-(Octadecyloxy)-5-(2,2-diphenyl-1-oxoethoxy)benzoic acid phenylmethyl ester

Diphenylacetyl chloride [from the reaction of 2.0 g (4.7 mmol) of diphenylacetic acid with thionyl chloride] dissolved in 20 ml of methylene chloride was added dropwise to an ice cooled solution of 2.0 g (4.0 mmol) of 3-hydroxy-5-(octadecyloxy)benzoic acid phenylmethyl ester and 1.1 ml (8 mmol) of triethylamine in 50 ml of methylene chloride with stirring. The reaction mixture was stirred with ice bath cooling for 1 hour, at room temperature for 20 hours and then was washed with 1N HCl and with NaHCO$_3$ solution. After drying, the solvent was removed at reduced pressure and the crude product was purified by chromatography on 50 g of silica gel using 10% ethyl acetate-hexane to give 2.5 g, mp 47°–49°, of 3-(octadecyloxy)-5-(2,2-diphenyl-1-oxoethoxy)benzoic acid phenylmethyl ester. The nmr and mass spectra were consistent with the structure.

EXAMPLE 11

3-(Octadecyloxy)-5-(2,2-diphenyl-1-oxoethoxy)benzoic acid

A mixture of 2.5 g of 3-(octadecyloxy)-5-(2,2-diphenyl-1-oxoethoxy)benzoic acid phenylmethyl ester and 0.5 g of 10% palladium on carbon in 75 ml of THF was stirred under a hydrogen atmosphere until uptake ceased after 5 hours. The catalyst was removed by filtration and the filtrate was concentrated at reduced pressure to a solid which was recrystallized from methanol-water to give 2.0 g, mp 82°–86°, of 3-(octadecyloxy)-5-(2,2-diphenyl-1-oxoethoxy)benzoic acid.

Anal. Calcd for $C_{39}H_{52}O_5$: C, 77.96; H, 8.72. Found: C, 77.63; H, 8.79.

EXAMPLE 12

3-(Octadecyloxy)-5-[(tricyclo[3.3.1./3,7/]dec-1-ylcarbonyl)oxy]benzoic acid phenylmethyl ester 1-Adamantane carboxylic acid chloride (0.067 g) in 1 ml of methylene chloride was added to a stirred solution of 0.153 g of 3-hydroxy-5-(octadecyloxy)benzoic acid phenylmethyl ester and 0.09 ml of triethylamine in 10 ml of methylene chloride. The reaction mixture was stirred at room temperature for 17 hours and was then washed with 1N HCl and with NaHCO$_3$ solution. After drying, the solvent was removed at reduced pressure and the crude product was purified by chromatography on 20 g of silica gel using 10% ethyl acetate-hexane to give 0.163 g of 3-(octadecyloxy)-5-[(tricyclo[3.3.1.1/3,7/]dec-1-ylcarbonyl)oxy]benzoic acid phenylmethyl ester as an oil. The nmr and mass spectra served to confirm the structure,

EXAMPLE 13

3-(Octadecyloxy)-5-[(tricyclo[3.3.1./3,7/]dec-1-ylcarbonyl)oxy]benzoic acid

A mixture of 0.16 g of 3-(octadecyloxy)-5-[(tricyclo[3.3.1./3,7/]dec-1-ylcarbonyl)oxy]benzoic acid phenylmethyl ester and 0.029 g of 10% palladium on carbon in 15 ml of THF was shaken under an initial hydrogen pressure of 54 psi in a Parr hydrogenator until uptake ceased after 2 hours. The usual workup followed by recrystallization from methanol-water gave 0.10 g, mp 44°–47°, of 3-(octadecyloxy)-5-[(tricyclo[3.3.1./3,7/]dec-1-ylcarbonyl)oxy]benzoic acid.

Anal. Calcd for $C_{36}H_{56}O_5$: C, 76.01; H, 9.92. Found: C, 76.15; H, 10.21.

EXAMPLE 14

3-[2-(2-Naphthalenyloxy)ethoxy]-5-(octadecyloxy)benzoic acid phenylmethyl ester

A mixture of 2.0 g (4 mmol) of 3-hydroxy-5-(octadecyloxy) benzoic acid phenylmethyl ester, 1.05 g 4.2 mmol) of 2-(2-bromoethoxy)naphthalene, 0.6 g (4 mmol) of sodium iodide and 1.1 g (8 mmol) of potassium carbonate in 60 ml of acetone and 15 ml of DMF was stirred at reflux for 49 hours. The solvents were removed at reduced pressure, water was added to the residue and the product was filtered. Recrystallization from methylene chloride-methanol gave 1.74 g, mp 62°–65°, of 3-[2-(2-naphthalenyloxy)ethoxy]-5-(octadecyloxy)benzoic acid phenylmethyl ester.

Anal. Calcd for $C_{44}H_{58}O_5$: C, 79.24; H, 8.77. Found: C, 78.90; H, 8.93.

EXAMPLE 15

3-[2-(2-Naphthalenyloxy)ethoxy]-5-(octadecyloxy) benzoic acid

A mixture of 1.74 g of 3-[2-(2-naphthalenyloxy)ethoxy]-5-(octadecyloxy)benzoic acid phenylmethyl ester and 1 g of 10% palladium on carbon was shaken under an initial hydrogen pressure of 54 psi in a Parr hydrogenator for 17 hours. The usual workup followed by recrystallization from methanol-water gave 1.18 g, mp 93°–94°, of 3-[2-(2-naphthalenyloxy)ethoxy]-5-(octadecyloxy)benzoic acid.

Anal. Calcd for $C_{37}H_{52}O_5$: C, 77.04; H, 9.09. Found: C, 76.81; H, 9.22.

EXAMPLE 16

3-(Octadecyloxy)-5-(3-phenoxypropoxy)benzoic acid phenylmethyl ester

A mixture of 12 g (0.024 mol) of 3-hydroxy-5-(octadecyloxy)-benzoic acid phenylmethyl ester, 6 ml (0.038 mol) of 3-phenoxy-propyl bromide, 3.6 g (0.024 mol) of sodium iodide and 10 g (0.072 mol) of potassium carbonate in 400 ml of acetone and 80 ml of DMF was stirred at reflux for 46 hours. The reaction mixture was filtered and the filtrate was concentrated to dryness at reduced pressure. Water was added to the residue and the product was extracted with ethyl acetate. The dried extract was concentrated at reduced pressure to an oil which was purified by HPLC using 5% ethyl acetate-hexane. The pure fractions were combined, triturated with hexane and filtered to give 14.6 g (96% yield, mp 46°–47°) of 3-(octadecyloxy)-5-(3-phenoxypropoxy)benzoic acid phenylmethyl ester. The structure was confirmed by nmr and mass spectra.

Anal. Calcd for $C_{41}H_{58}O_5$: C, 78.05; H, 9.27. Found: C, 77.89; H, 9.03.

EXAMPLE 17

3-(Octadecyloxy)-5-(3-phenoxypropoxy)benzoic acid

A mixture of 14.6 g of 3-(octadecyloxy)-5-(3-phenoxypropoxy) benzoic acid phenylmethyl ester and 3 g of 10% palladium on carbon was shaken in a hydrogen atmosphere at room temperature for 2 hours. The catalyst was removed by filtration and the filtrate was concentrated to a solid which was recrystallized from ether-hexane to give 11.8 g (95% yield, mp 79°–81°) of 3-(octadecyloxy)-5-(3-phenoxypropoxy)benzoic acid.

Anal. Calcd for $C_{34}H_{52}O_5$: C, 75.52; H, 9.69. Found: C, 75.09; H, 9.80.

EXAMPLE 18

3-[[6-[2,3-bis(Phenylmethoxy)phenyl]hexyl]oxy]-5-(octadecyloxy)benzoic acid phenylmethyl ester A mixture of 1.5 g (3 mmol) of 3-hydroxy-5-(octadecyloxy) benzoic acid phenylmethyl ester, 1.6 g (3.4 mmol) of 1-(6-bromo-hexyl)-2,3-bis(phenylmethoxy)-benzene [M. Carson, R.-J. Han and R. A. LeMahieu, U.S. Pat. No. 5,025,036 (1991)], 0.45 g (3 mmol) of potassium iodide and 0.84 g (6 mmol) of potassium carbonate in 40 ml of acetone and 10 ml of DMF was stirred at reflux for 47 hours. The solvents were removed at reduced pressure and the residue was purified by HPLC using 5% ethyl acetate-hexane to give 2.0 g (77% yield) of 3-[[6-[2,3-bis(phenylmethoxy)phenyl]-hexyl]oxy]-5-(octadecyloxy)benzoic acid phenylmethyl ester as an oil. The nmr spectrum served to confirm the structure.

EXAMPLE 19

3-[[6-(2,3-Dihydroxyphenyl)hexyl]oxy]-5-(octadecyloxy) benzoic acid

A mixture of 2.0 g of 3-[[6-[2,3-bis(phenylmethoxy)-phenyl]hexyl]oxy]-5-(octadecyloxy)benzoic acid phenylmethyl ester and 0.5 g of 10% palladium on carbon in 100 ml of THF was stirred in a hydrogen atmosphere until uptake ceased after 5 hours. The usual workup followed by trituration of the crude product with hexane gave 1.2 g (88% yield, mp 92°–94°) of 3-[[6-(2,3-dihydroxyphenyl) hexyl]oxy]-5-(octadecyloxy)benzoic acid.

Anal. Calcd for $C_{37}H_{58}O_6$: C, 74.21; H, 9.76. Found: C, 74.27; H, 9.55.

EXAMPLE 20

3-[(4-Methylthio)phenoxy]propyl bromide

A mixture of 10 g of 4-(methylmercapto)phenol, 72 ml of 1,3-dibromopropane and 30 g of potassium carbonate in 150 ml of acetone and 25 ml of DMF was stirred at reflux for 24 hours. The usual workup followed by purification by HPLC using 2% ethyl acetate-hexane gave 5.6 g (30% yield, mp 33°–35°) of 3-[(4-methyl-thio)phenoxy]propyl bromide.

Anal. Calcd for $C_{10}H_{13}BrOS$: C, 45.99; H, 5.02; Br, 30.59; S, 12.28. Found: C, 46.08; H, 4.89; Br, 30.86; S, 12.07.

EXAMPLE 21

3-[(4-Methylsulfinyl)phenoxy]propyl bromide

To 2.0 g (7.66 mmol) of 3-[(4-methylthio)phenoxy]-propyl bromide in 100 ml of methanol a solution of 1.65 g (7.66 mmol) of sodium periodate in 10 ml of water was added dropwise over 10 minutes. The reaction mixture was stirred at room temperature for 4 days. The solvent was removed at reduced pressure, water was added to the residue and the product was extracted with ethyl acetate. The dried extract was concentrated to an oil which was triturated with hexane and filtered to give 1.93 g (91% yield, mp<30°) of 3-[(4-methylsulfinyl)-phenoxy]propyl bromide.

Anal. Calcd for $C_{10}H_{13}BrO_2S$: C, 43.33; H, 4.73; Br, 28.83: S, 11.59. Found: C, 42.70; H, 4.74; Br, 28.81; S, 11.53.

EXAMPLE 22

3-[(4-Methylsulfonyl)phenoxy]propyl bromide

To 2.0 g (7.66 mmol) of 3-[(4-methylthio)phenoxy]-propyl bromide in 75 ml of methylene chloride cooled in an ice bath was added in portions with stirring 2.9 g of 80% 3-chloroperbenzoic acid. After stirring at room temperature for 4 days, 1.5 g of 80% 3-chloroperbenzoic acid was added and stirring was continued for 24 hours. The reaction mixture was filtered and the filtrate was washed with $NaHCO_3$ solution. The dried extract was concentrated to a solid which was recrystallized from ether-hexane to give 1.98 g (93% yield, mp 91°–93°) of 3-[(4-methylsulfonyl)phenoxy]propyl bromide.

Calcd for $C_{10}H_{13}BrO_3S$: C, 40.97; H, 4.47; Br, 27.26; S, 10.94; Found: C, 40.85; H, 4.38; Br, 27.56; S, 10.64.

EXAMPLE 23

3-[3-[4-(Methylsulfinyl)phenoxy]propoxy]-5-(octadecyloxy)benzoic acid methyl ester A mixture of 0.8 g (1.9 mmol) of 3-hydroxy-5-(octadecyloxy) benzoic acid methyl ester, 0.63 g (2.28 mmol) of 3-[(4-methyl-sulfinyl)phenoxy]propyl bromide and 1 g (7.2 mmol) of potassium carbonate in 40 ml of acetone and 10 ml of DMF was stirred at reflux for 24 hours. The usual workup and recrystallization from ethyl acetate gave 0.8 g (68% yield, mp 86°–88°) of 3-[3-[4-(methylsulfinyl)phenoxy]propoxy]-5-(octadecyloxy)benzoic acid methyl ester.

Anal. Calcd for $C_{36}H_{56}SO_6$: C, 70.07; H, 9.15; S, 5.20. Found: C, 69.85; H, 9.24; S, 4.94.

EXAMPLE 24

3-[3-[4-(Methylsulfinyl)phenoxy]propoxy]-5-(octadecyloxy)benzoic acid

Sodium hydroxide hydrolysis of 3-[3-[4-(methylsulfinyl) phenoxy]propoxy]-5-(octadecyloxy)benzoic acid methyl ester as in earlier Examples gave 3-[3-[4-(methylsulfinyl)phenoxy]propoxy]-5-(octadecyloxy)benzoic acid (88% yield, mp 77°–80°).

Anal. Calcd for $C_{35}H_{54}O_6S$: C, 69.73; H, 9.03; S, 5.23. Found: C, 69.86; H, 9.20; S, 5.24.

EXAMPLE 25

3-[3-[4-(Methylsulfonyl)phenoxy]propoxy]-5-(octadecyloxy)benzoic acid methyl ester A mixture of 0.8 g (1.9 mmol) of 3-hydroxy-5-(octadecyloxy) benzoic acid methyl ester, 0.668 g (2.28 mmol) of 3-[(4-methylsulfonyl)phenoxy]propyl bromide and 1 g (7.6 mmol) of potassium carbonate in 40 ml of acetone and 10 ml of DMF was stirred at reflux for 24 hours. The usual workup and recrystallization from ethyl acetate gave 1.1 g (92% yield, mp 101°–102°) of 3-[3-[4-(methylsulfonyl)phenoxy]propoxy]-5-(octadecyloxy)benzoic acid methyl ester.

Anal. Calcd for $C_{36}H_{56}SO_7$: C, 68.32; H, 8.92; S, 5.07. Found: C, 68.22; H, 9.12; S, 4.85.

EXAMPLE 26

3-[3-[4-(Methylsulfonyl)phenoxy]propoxy]-5-(octadecyloxy)benzoic acid

Sodium hydroxide hydrolysis of 3-[3-[4-(methylsulfonyl) phenoxy]propoxy]-5-(octadecyloxy)benzoic acid methyl ester as in earlier Examples gave 3-[3-[4-(methylsulfonyl)phenoxy]propoxy]-5-(octadecyloxy)benzoic acid (77% yield, mp 110°–111°).

Anal. Calcd for $C_{35}H_{54}O_7S$: C, 67.93; H, 8.80; S, 5.18. Found: C, 67.93; H, 8.90; S, 5.29.

EXAMPLE 27

3-Hydroxy-5-(octadecyloxy)benzoic acid methyl ester

A mixture of 5.0 g (0.03 mol) of 3,5-dihydroxybenzoic acid methyl ester, 9.9 g (0.03 mol) of 1-bromooctadecane and 4.1 g (0.03 mol) of potassium carbonate in 100 ml of acetone and 5 ml of DMF was stirred at reflux for 24 hours. The solvents were removed at reduced pressure and the residue was stirred with ethyl acetate and filtered to remove inorganic salts. The filtrate was concentrated to dryness and the residue was stirred with 500 ml of methylene chloride and filtered to remove the residual 3,5-dihydroxybenzoic acid methyl ester. The filtrate was concentrated and purified by chromatography on 300 g of silica gel using 5% ethyl acetate-toluene to give 4.07 g (33% yield, mp 93°–94°) of 3-hydroxy-5-(octadecyloxy) benzoic acid methyl ester.

EXAMPLE 28

3-[(4-Phenylmethoxy)phenoxy]propyl bromide

A mixture of 10 g (0.05 mol) of 4-benzyloxyphenol, 51 ml (0.5 mol) of 1,3-dibromopropane and 20.7 g (0.15 mol) of potassium carbonate in 150 ml of acetone was stirred at reflux for 24 hours. The solvent and excess 1,3-dibromopropane were removed at reduced pressure and the residue was crystallized from methanol to give 10 g (63% yield, mp 53°–56°) of 3-[(4-phenylmethoxy)phenoxy]propyl bromide.

EXAMPLE 29

3-[[3-(4-Phenylmethoxy)phenoxy]propoxy]-5-(octadecyloxy)benzoic acid methyl ester A mixture of 4.0 g (9.5 mmol) of 3-hydroxy-5-(octadecyloxy) benzoic acid methyl ester, 3.05 g (9.5 mmol) 3-[(4-phenylmethoxy)phenoxy]propyl bromide, 1.43 g (9.5 mmol) of sodium iodide and 2.67 g (19 mmol) of potassium carbonate in 100 ml of acetone and 25 ml of DMF was stirred at reflux for 43 hours. The usual workup followed by recrystallization from methylene chloride gave 4.85 g (77% yield, mp 75°–77°) of 3-[[3-(4-phenylmethoxy) phenoxy]propoxy]-5-(octadecyloxy)-benzoic acid methyl ester.

Anal. Calcd for $C_{42}H_{60}O_6$: C, 76.33; H, 9.15. Found: C, 76.04; H, 9.09.

EXAMPLE 30

3-[[3-(4-Phenylmethoxy)phenoxy]propoxy]-5-(octadecyloxy)benzoic acid

Sodium hydroxide hydrolysis of 3-[[3-(4-phenylmethoxy) phenoxy]propoxy]-5-(octadecyloxy)benzoic acid methyl ester gave 3-[[3-(4-phenylmethoxy)phenoxy]propoxy]-5-(octadecyloxy)benzoic acid (99% yield, mp 99°–101°)

Anal. Calcd for $C_{41}H_{58}O_6$: C, 76.12; H, 9.04. Found: C, 75.92; H, 9.02.

EXAMPLE 31

3-[3-(4-Hydroxyphenoxy)propoxy]-5-(octadecyloxy) benzoic acid

A mixture of 0.30 g of 3-[[3-(4-phenylmethoxy)-phenoxy]propoxy]-5-(octadecyloxy)benzoic acid and 0.1 g of 10% palladium on carbon in 25 ml of THF was stirred in a hydrogen atmosphere until uptake ceased after 2 hours. The usual workup followed by recrystallization from ether-hexane gave 0.217 g (84% yield, mp 92°–95°) of 3-[3-(4-hydroxyphenoxy)propoxy]-5-(octadecyloxy)benzoic acid.

Anal. Calcd for $C_{34}H_{52}O_6$: C, 73.35; H, 9.41. Found: C, 73.07; H, 9.43

EXAMPLE 32

3-Hydroxy-5-[3-[4-(phenylmethoxy)phenoxy]propoxy]-benzoic acid methyl ester

A mixture of 2.0 g (11.9 mmol) of 3,5-dihydroxybenzoic acid methyl ester, 3.8 g (11.9 mmol) of 3-[(4-phenylmethoxy)phenoxy]propyl bromide and 1.7 g (12.3 mmol) of potassium carbonate in 40 ml of acetone and 2 ml of DMF was stirred at reflux for 24 hours. The solvents were removed at reduced pressure, the residue was stirred with methylene chloride and filtered. The filtrate was concentrated to a solid which was recrystallized from methylene chloride-methanol to give 1.77 g, mp 134°–136°, of 3,5-bis[3-[4-(phenylmethoxy)phenoxy]propoxy]benzoic acid methyl ester. The filtrate was concentrated to a solid which was purified by chromatography on 20 g of silica gel (230–400 mesh) using 10% ethyl acetate-hexane to give 1.47 g (30% yield, mp 120°–122°) of 3-hydroxy-5-[3-[4-(phenylmethoxy)-phenoxy]propoxy]benzoic acid methyl ester.

Anal. Calcd for $C_{24}H_{24}O_6$: C, 70.58; H, 5.92. Found: C, 70.86; H, 5.72.

EXAMPLE 33

3-(Octadecyloxy)-5-[3-[4-(phenylmethoxy)phenoxy]-propoxy]benzoic acid methyl ester A mixture of 11 g (27 mmol) of 3-hydroxy-5-[3-[4-(phenyl-methoxy)phenoxy]propoxy]benzoic acid methyl ester, 9.9 g (29.6 mmol) of 1-bromooctadecane and 7.5 g (55 mmol) of potassium carbonate in 225 ml of DMF was stirred and heated at 80° for 30 hours. The solvent was removed at reduced pressure and the residue was purified by chromatography on 300 g of silica gel using 10% ethyl acetate-hexane to give 15.7 g (88% yield, mp 76°–77°) of 3-(octadecyloxy)-5-[3-[4-(phenylmethoxy)phenoxy]propoxy]benzoic acid methyl ester.

EXAMPLE 34

3-[3-(4-Hydroxyphenoxy)propoxy]-5-(octadecyloxy) benzoic acid methyl ester

A mixture of 0.40 g of 3-(octadecyloxy)-5-[3-[4-(phenylmethoxy) phenoxy]propoxy]benzoic acid methyl ester and 0.1 g of 10% palladium on carbon in 25 ml of THF was stirred in a hydrogen atmosphere for 4 hours. The usual workup followed by purification by chromatography on 12 g of silica gel (230–400 mesh) using 20% ethyl acetate-hexane to give 0.177 g (51% yield, mp 85°–88°) of 3-[3-(4-hydroxyphenoxy)propoxy]-5-(octadecyloxy)benzoic acid methyl ester.

Anal. Calcd for $C_{35}H_{54}O_6$: C, 73.65; H, 9.54. Found: C, 73.81; H, 9.73.

EXAMPLE 35

3-[3-[4-(Phenylmethoxy)phenoxy]propoxy]-5-(tetradecyloxy)benzoic acid methyl ester A mixture of 1.0 g (2.45 mmol) of 3-hydroxy-5-[3-[4-(phenylmethoxy)phenoxy]propoxy]benzoic acid methyl ester, 0.73 ml (2.69 mmol) of 1-bromotetradecane and 0.7 g (4.9 mmol) of potassium carbonate in 20 ml of anhydrous DMF was stirred and heated at 80° for 22 hours. The usual workup followed by chromatography on 30 g of silica gel using 10% ethyl acetate-hexane, trituration of the combined pure fractions with methanol and filtration gave 1.37 g (93% yield, mp 69°-70°) of 3-[3-[4-(phenylmethoxy)phenoxy]propoxy]-5-(tetradecyloxy)benzoic acid methyl ester.

EXAMPLE 36

3-[3-[4-(Phenylmethoxy)phenoxy]propoxy]-5-(tetradecyloxy)benzoic acid

Sodium hydroxide hydrolysis of 3-[3-[4-(phenylmethoxy) phenoxy]propoxy]-5-(tetradecyloxy)benzoic acid methyl ester gave 3-[3-[4-(phenylmethoxy)phenoxy]propoxy]-5-(tetradecyloxy)benzoic acid (96% yield, mp 77°-79°).

Anal. Calcd for $C_{37}H_{50}O_6$: C, 75.22; H, 8.53. Found: C, 74.90; H, 8.62.

EXAMPLE 37

3-[3-(4-Hydroxyphenoxy)propoxy]-5-(tetradecyloxy) benzoic acid

Catalytic hydrogenolysis of 3-[3-[4-(phenylmethoxy)-phenoxy]propoxy]-5-(tetradecyloxy)benzoic acid as described in earlier Examples gave 3-[3-(4-hydroxyphenoxy)propoxy]-5-(tetradecyloxy) benzoic acid (92% yield, mp 91°-93°).

Anal. Calcd for $C_{30}H_{44}O_6$: C, 71.97; H, 8.86. Found: C, 72.08: H, 9.00.

EXAMPLE 38

3-(Decyloxy)-5-[3-[4-(phenylmethoxy)phenoxy]-propoxy]benzoic acid methyl ester

A mixture of 1.0 g (2.45 mmol) of 3-hydroxy-5-[3-[4-(phenylmethoxy)phenoxy]propoxy]benzoic acid methyl ester, 0.6 ml (2.69 mmol) of 1-bromodecane and 0.7 g (4.9 mmol) of potassium carbonate in 20 ml of DMF was stirred at 80° for 24 hours. The usual workup followed by recrystallization from ether-hexane gave 1.25 g (93% yield, mp 68°-70°) of 3-(decyloxy)-5-[3-[4-(phenylmethoxy) phenoxy]propoxy]benzoic acid methyl ester.

EXAMPLE 39

3-(Decyloxy)-5-[3-[4-(phenylmethoxy)phenoxy]-propoxy]benzoic acid

Sodium hydroxide hydrolysis of 3-(decyloxy)-5-[3-[4-(phenylmethoxy)phenoxy]propoxy]benzoic acid methyl ester gave 3-(decyloxy)-5-[3-[4-(phenylmethoxy)phenoxy]propoxy]benzoic acid (95% yield, mp 107°-109°)

Anal. Calcd for $C_{33}H_{42}O_6$: C, 74.13; H, 7.92. Found: C, 73.97; H, 8.16.

EXAMPLE 40

3-(Decyloxy)-5-[3-(4-hydroxyphenoxy)propoxy]benzoic acid

Catalytic hydrogenolysis of 3-(decyloxy)-5-[3-[4-(phenylmethoxy) phenoxy]propoxy]benzoic acid gave 3-(decyloxy)-5-[3-(4-hydroxyphenoxy)propoxy]benzoic acid (77% yield, mp 106°-109°).

Anal. Calcd for $C_{26}H_{36}O_6$: C, 70.24; H, 8.16. Found: C, 70.10; H, 8.14.

EXAMPLE 41

3,5-bis[3-[4-(Phenylmethoxy)phenoxy]propoxy]benzoic acid

A solution of 1.5 g (2.3 mmol) of 3,5-bis[3-[4-(phenylmethoxy) phenoxy]propoxy]benzoic acid methyl ester (prepared in Example 46) and 1.2 ml (7.2 mmol) of 6N NaOH in 25 ml of methanol and 10 ml of dioxane was stirred at reflux under argon for 19 hours. The solvents were removed at reduced pressure, the residue was acidified and the product was extracted with ethyl acetate. The dried extract was concentrated to a solid which was recrystallized from acetone-hexane to give 1.37 g (93% yield, mp 139°-140°) of 3,5-bis[3-[4-(phenylmethoxy)phenoxy]propoxy]benzoic acid.

Anal. Calcd for $C_{39}H_{38}O_8$: C, 73.80; H, 6.03. Found: C, 73.69; H, 6.20.

EXAMPLE 42

3,5-bis[3-(4-Hydroxyphenoxy)propoxy]benzoic acid

Catalytic hydrogenolysis under the usual conditions of 3,5-bis[3-[4-(phenylmethoxy)phenoxy]propoxy]benzoic acid gave 3,5-bis[3-(4-hydroxyphenoxy)propoxy]-benzoic acid (94% yield, mp 160°-162°).

Anal. Calcd for $C_{25}H_{26}O_8$: C, 66.07; H, 5.77. Found: C, 65.94; H, 5.64.

EXAMPLE 43

3-(Octadecyloxy)-5-[[6-[4-(phenylmethoxy)phenoxy]-hexyl]oxy]benzoic acid phenylmethyl ester A mixture of 0.60 (1.2 mmol) of 3-hydroxy-5-(octadecyloxy) benzoic acid phenylmethyl ester, 0.46 g (1.27 mmol) of 6-[(4-phenylmethoxy)phenoxy]hexyl bromide and 0.3 g (2.17 mmol) of potassium carbonate in 20 ml of acetone and 1 ml of DMF was stirred at reflux for 21 hours. The usual workup followed by chromatography on 40 g of silica gel (230–400 mesh) using 5% ethyl acetate-hexane gave 0.7 g (74% yield, mp 60°-62°) of 3-(octadecyloxy)-5-[[6-[4-(phenylmethoxy)phenoxy]hexyl]oxy]benzoic acid phenylmethyl ester.

EXAMPLE 44

3-[[6-(4-Hydroxyphenoxy)hexyl]oxy]-5-(octadecyloxybenzoic acid

Catalytic hydrogenolysis of 3-(octadecyloxy)-5-[[6-[4-(phenylmethoxy)phenoxy]hexyl]oxy]benzoic acid phenylmethyl ester gave 3-[[6-(4-hydroxyphenoxy)hexyl]oxy]-5-(octadecyloxybenzoic acid, mp 104°-105°.

Anal. Calcd for $C_{37}H_{58}O_6$: C, 74.21; H, 9.76. Found: C, 74.24; H, 9.98.

EXAMPLE 45

3-(Octadecyloxy)-5-[3-[2-(phenylmethoxy)phenoxy]-propoxy]benzoic acid phenylmethyl ester A mixture of 0.6 g (1.2 mmol) of 3-hydroxy-5-(octadecyloxy) benzoic acid phenylmethyl ester, 0.3 g (2.17 mmol) of 3-[(2-phenylmethoxy)phenoxy]propyl bromide and 0.3 g (2.17 mmol) of potassium carbonate in 20 ml of acetone and 1 ml of DMF was stirred at reflux for 23 hours. The usual workup followed by chromatography on 40 g of silica gel (230–400 mesh) using 5% ethyl acetate-hexane gave 0.6 g (67% yield, mp 49°–50°) of 3-(octadecyloxy)-5-[3-[2-(phenylmethoxy)phenoxy]-propoxy]benzoic acid phenylmethyl ester.

EXAMPLE 46

3-[3-(2-Hydroxyphenoxy)propoxy]-5-(octadecyloxy) benzoic acid

Catalytic hydrogenolysis of 3-(octadecyloxy)-5-[3-[2-(phenylmethoxy)phenoxy]propoxy]benzoic acid phenylmethyl ester gave 3-[3-(2-hydroxyphenoxy)propoxy]-5-(octadecyloxy)benzoic acid, mp 75°–77°.

Anal. Calcd for $C_{34}H_{52}O_6$: C, 73.35; H, 9.41. Found: C, 73.16; H, 9.66.

EXAMPLE 47

2-Hydroxy-5-(octadecyloxy)benzoic acid methyl ester

A mixture of 1 g (5.95 mmol) of 2,5-dihydroxybenzoic acid methyl ester, 1.98 g (5.95 mmol) of 1-bromooctadecane and 0.825 g (5.95 mmol) of potassium carbonate in 20 ml of acetone and 1 ml of DMF was stirred at reflux for 20 hours. The usual workup followed by purification by HPLC using 1% ethyl acetate-hexane gave 1.8 (72% yield, mp 61°–64°) of 2-hydroxy-5-(octadecyloxy)benzoic acid methyl ester.

EXAMPLE 48

5-(Octadecyloxy)-2-[3-[4-(phenylmethoxy)phenoxy]-propoxy]benzoic acid methyl ester A mixture of 1 g (2.4 mmol) of 2-hydroxy-5-(octadecyloxy) benzoic acid methyl ester, 0.85 g (2.6 mmol) of 3-[(4-phenylmethoxy)phenoxy]propyl bromide and 0.65 g (4.7 mmol) of potassium carbonate in 40 ml of acetone and 7 ml of DMF was stirred at reflux for 48 hours. The usual workup followed by recrystallization from ethyl acetate-hexane gave 1.2 g (76% yield, mp 81°–83°) of 5-(octadecyloxy)-2-[3-[4-(phenylmethoxy)phenoxy]propoxy]benzoic acid methyl ester.

Anal. Calcd for $C_{42}H_{60}O_6$: C, 76.12; H, 9.04. Found: C, 75.96; H, 9.23.

EXAMPLE 49

5-(Octadecyloxy)-2-[3-[4-(phenylmethoxy)phenoxy]-propoxy]benzoic acid

Hydrolysis with sodium hydroxide of 5-(octadecyloxy)-2-[3-[4-(phenylmethoxy)phenoxy]propoxy]benzoic acid methyl ester gave 5-(octadecyloxy)-2-[3-[4-(phenylmethoxy)phenoxy]propoxy]benzoic acid, mp 93°–95°.

Anal. Calcd for $C_{41}H_{58}O_6$: C, 76.12; H, 9.04. found: C, 75.96; H, 9.23.

EXAMPLE 50

2-[3-(4-Hydroxyphenoxy)propoxy]-5-(octadecyloxy) benzoic acid

Catalytic hydrogenolysis of 5-(octadecyloxy)-2-[3-[4-(phenylmethoxy)phenoxy]propoxy]benzoic acid gave 2-[3-(4-hydroxyphenoxy)propoxy]-5-(octadecyloxy)-benzoic acid, mp 98°–100°.

Anal. Calcd for $C_{34}H_{52}O_6$: C, 73.35; H, 9.41. Found: C, 73.16; H, 9.42.

EXAMPLE 51

2-Hydroxy-4-(octadecyloxy)benzoic acid methyl ester

A mixture of 1 g (5.95 mmol) of 2,4-dihydroxybenzoic acid methyl ester, 1.98 g (5.95 mmol) of 1-bromooctadecane and 0.825 g (5.95 mmol) of potassium carbonate was stirred at reflux for 40 hours in 20 ml of acetone and 2 ml of DMF. The usual workup followed by purification by HPLC using 1% ethyl acetate-hexane gave 2-hydroxy -4-(octadecyloxy)benzoic acid methyl ester, mp 61°–64°.

EXAMPLE 52

4-(Octadecyloxy)-2-[3-[4-(phenylmethoxy)phenoxy]-propoxy]benzoic acid methyl ester A mixture of 1 g (2.4 mmol) of 2-hydroxy-4-(octadecyloxy) benzoic acid methyl ester, 0.9 g (2.8 mmol) of 3-[(4-phenylmethoxy) phenoxy]propyl bromide and 1.2 g (8.7 mmol) of potassium carbonate in 40 ml of acetone and 10 ml of DMF was stirred at reflux for 44 hours. The usual workup followed by chromatography on 30 g of silica gel using 10% ethyl acetate-hexane gave 1.3 g, mp 68°–70°, of 4-(octadecyloxy)-2-[3-[4-(phenylmethoxy)phenoxy]propoxy]benzoic acid methyl ester.

EXAMPLE 53

4-(Octadecyloxy)-2-[3-[4-(phenylmethoxy)phenoxy]-propoxy]benzoic acid

Sodium hydroxide hydrolysis of 4-(octadecyloxy)-2-[3-[4-(phenylmethoxy)phenoxy]propoxy]benzoic acid methyl ester gave 4-(octadecyloxy)-2-[3-[4-(phenylmethoxy)phenoxy]propoxy]benzoic acid (88% yield, mp 102°–104°).

Anal. Calcd for $C_{41}H_{58}O_6$: C, 76.12; H, 9.04. Found: C, 76.08; H, 9.16.

EXAMPLE 54

2-[3-(4-Hydroxyphenoxy)propoxy]-4-(octadecyloxy) benzoic acid

Catalytic hydrogenolysis of 4-(octadecyloxy)-2-[3-[4-(phenylmethoxy)phenoxy]propoxy]benzoic acid gave 2-[3-(4-hydroxyphenoxy)propoxy]-4-(octadecyloxy)-benzoic acid (62% yield, mp 97°–100°).

Anal. Calcd for $C_{34}H_{52}O_6$: C, 73.35; H, 9.41. Found: C, 73.40; H, 9.54.

EXAMPLE 55

2-Hydroxy-3-(octadecyloxy)benzoic acid methyl ester

A mixture of 1.0 g (5.95 mmol) of 2,3-dihydroxybenzoic acid methyl ester, 1.98 g (5.95 mmol) of 1-bromooctadecane and 0.825 g (5.95 mmol) of potassium carbonate in 20 ml of acetone and 4 ml of DMF was stirred at reflux for 40 hours. The usual workup followed by purification by chromatography on 40 g of silica gel (230–400 mesh) using 50% toluene-hexane gave 0.40 g (16% yield, mp 57°–60°) of 2-hydroxy-3-(octadecyloxy)benzoic acid methyl ester. The structure was established by nmr and mass spectra.

EXAMPLE 56

3-(Octadecyloxy)-2-[3-[4-(phenylmethoxy)phenoxy]propoxy]benzoic acid methyl ester A mixture of 0.40 g (0.95 mmol) of 2-hydroxy-3-(octadecyloxy) benzoic acid methyl ester, 0.365 g (1.14 mmol) of 3-[(4-phenylmethoxy)phenoxy]propyl bromide and 0.60 g 4.35 mmol) of potassium carbonate in 20 ml of acetone and 5 ml of DMF was stirred at reflux for 44 hours. The usual workup followed by chromatography on 30 g of silica gel (230–400 mesh) using 10% ethyl acetate-hexane gave 0.50 g (79% yield, mp 43°–45°) of 3-(octadecyloxy)-2-[3-[4-(phenylmethoxy)phenoxy]propoxy]benzoic acid methyl ester.

EXAMPLE 57

3-(Octadecyloxy)-2-[3-[4-(phenylmethoxy)phenoxy]propoxy]benzoic acid

Sodium hydroxide hydrolysis of 3-(octadecyloxy)-2-[3-[4-(phenylmethoxy)phenoxy]propoxy]benzoic acid methyl ester gave 3-(octadecyloxy)-2-[3-[4-(phenylmethoxy)phenoxy]propoxy]benzoic acid (76% yield, mp 75°–76°).

Anal. Calcd for $C_{41}H_{58}O_6$: C, 76;12; H, 9.04. Found: C, 75.88; H. 9.25.

EXAMPLE 58

2-[3-(4-Hydroxyphenoxy)propoxy]-3-(octadecyloxy)benzoic acid

Catalytic hydrogenolysis of 3-(octadecyloxy)-2-[3-[4-(phenylmethoxy)phenoxy]propoxy]benzoic acid gave 2-[3-(4-hydroxyphenoxy)propoxy]-3-(octadecyloxy)-benzoic acid (77% yield, mp 81°–83°).

Anal. Calcd for $C_{34}H_{52}O_6$: C, 73.35; H, 9.441. Found: C, 73.27; H, 9.47.

EXAMPLE 59

3-Hydroxy-5-(tetradecyloxy)benzoic acid methyl ester

A mixture of 10 g (0.06 mol) of 3,5-dihydroxybenzoic acid methyl ester, 16.2 ml (0.06 mol) of 1-bromotetradecane and 8.2 g (0.06 mol) of potassium carbonate in 200 ml of acetone and 20 ml of DMF was stirred at reflux under argon for 24 hours, After the usual workup, the crude product was triturated with hot methylene chloride and filtered. The filtrate was concentrated at reduced pressure and the solid residue was recrystallized from methylene chloride-methanol to give the 3,5-dialkylated product. The filtrate was concentrated and the residue was purified by HPLC using 15% ethyl acetatehexane to give 7.3 g (34% yield, mp 92°–94°) of 3-hydroxy-5-(tetradecyloxy)benzoic acid methyl ester. The nmr spectra was consistent with the structure.

EXAMPLE 60

3-[[6-[2,3-bis(Phenylmethoxy)phenyl]hexyl]oxy]-5-(tetra-decyloxy)benzoic acid methyl ester A mixture of 1.5 g (4.1 mmol) of 3-hydroxy-5-(tetradecyloxy) benzoic acid methyl ester, 2.3 g (5.1 mmol) of 1-(6-bromohexyl)-2,3-bis(phenylmethoxy)benzene, 1.1 g (8.2 mmol) of potassium carbonate and 0.6 g (4.1 mmol) of sodium iodide in 50 ml of acetone and 15 ml of DMF was stirred at reflux under argon for 32 hours. After the usual workup, the crude product was crystallized from methylene chloride-methanol to give 2.8 g (93% yield, mp 56°–58°) of 3-[[6-[2,3-bis(phenylmethoxy)phenyl]hexyl]oxy]-5-(tetradecyloxy) benzoic acid methyl ester.

Anal. Calcd for $C_{48}H_{64}O_6$: C, 78.22; H, 8.75. Found: C, 77.99; H, 8.66.

EXAMPLE 61

3-[[6-(2,3-Dihydroxyphenyl)hexyl]oxy]-5-(tetradecyloxy) benzoic acid methyl ester A mixture of 1.0 g of 3-[[6-[2,3-bis(phenylmethoxy)phenylhexyl]oxy]-5-(tetradecyloxy)benzoic acid methyl ester and 0.4 g of 10% palladium on carbon in 100 ml of THF was stirred in a hydrogen atmosphere until uptake ceased after 3.5 hours. After the usual workup, the crude product was triturated with hexane and filtered to give 0.65 g (86% yield, mp 77°–79°) of 3-[[6-(2,3-dihydroxyphenyl) hexyl]oxy]-5-(tetradecyloxy)benzoic acid methyl ester.

Anal. Calcd for $C_{34}H_{52}O_6$: C, 73.35; H, 9.41. Found: C, 73.53; H, 9.29.

EXAMPLE 62

3-[[6-[2,3-bis(Phenylmethoxy)phenyl]hexyl]oxy]-5-(tetradecyloxy)benzoic acid

A solution of 1.78 g (2.3 mmol) of 3-[[6-[2,3-bis(-phenylmethoxy) hexyl]oxy]-5-(tetradecyloxy)benzoic acid methyl ester and 1.2 ml (7.2 mmol) of 6N NaOH in 75 ml of methanol and 25 ml of dioxane was stirred at reflux under argon for 20 hours. After the usual workup, 1.67 g (mp 75°–77°), of 3-[[6-[2,3-bis(phenylmethoxy) phenyl]hexyl]oxy]-5-(tetradecyloxy)benzoic acid was obtained.

EXAMPLE 63

3-[[6-(2,3-dihydroxyphenyl)hexyl]oxy]-5-(tetradecyloxy)benzoic acid

A mixture of 1.66 g of 3-[[6-[2,3-bis(phenylmethoxy)-phenyl]hexyl]oxy]-5-(tetradecyloxy)benzoic acid and 0.3 g of 10% palladium on carbon in 75 ml of THF was stirred in a hydrogen atmosphere until uptake ceased after 4 hours. The usual workup followed by trituration with hexane and filtration gave 1.14 g (91% yield, mp 92°–94°) of 3-[[6-(2,3-dihydroxyphenyl)hexyl]oxy]-5-(tetradecyloxy) benzoic acid.

Anal. Calcd for $C_{33}H_{50}O_6$: C, 73.03; H, 9.29. Found: C, 73.05; H, 9.21.

EXAMPLE 64

3-(Decyloxy)-5-hydroxybenzoic acid methyl ester

A mixture of 10.0 g (0.06 mol) of 3,5-dihydroxybenzoic acid methyl ester, 12.3 ml (0.06 mol) of 1-bromodecane and 8.2 g (0.06 mol) of potassium carbonate in 200 ml of acetone and 20 ml of DMF was stirred at reflux under argon for 24 hours. After the usual workup, purification by HPLC using 15% ethyl acetate-hexane gave 7.3 g (34% yield, mp 92°–94°) of 3-(decyloxy)-5-hydroxybenzoic acid methyl ester. The nmr spectra was consistent with the structure.

EXAMPLE 65

3-(Decyloxy)-5-[[6-[2,3-bis(phenylmethoxy)phenyl]hexyl]oxy]benzoic acid methyl ester A mixture of 1.5 g (4.86 mmol) of 3-(decyloxy)-5-hydroxybenzoic acid methyl ester, 2.2 g (4.86 mmol) of 1-(6-bromohexyl)-2,3-bis (phenylmethoxy)benzene, 1.3 g (9.7 mmol) of potassium carbonate and 0.73 g (4.86 mmol) of sodium iodide in 50 ml of acetone and 15 ml of DMF was stirred at reflux for 48 hours. After the usual workup, the crude product was purified by HPLC using 10% ethyl acetate-hexane to give 2.47 g (75% yield, mp 45°–46°) of 3-(decyloxy)-5-[[6-[2,3-bis(phenylmethoxy)phenyl]hexyl]oxy]benzoic acid methyl ester.

Anal. Calcd for $C_{44}H_{56}O_6$: C, 77.61; H, 8.29. Found: C, 77.68; H, 8.41.

EXAMPLE 66

3-(Decyloxy)-5-[[6-(2,3-dihydroxyphenyl)hexyl]oxy]benzoic acid methyl ester

A mixture of 0.7 g of 3-(decyloxy)-5-[[6-[2,3-bis(phenylmethoxy) phenyl]hexyl]oxy]benzoic acid methyl ester and 0.3 g of 10% palladium on carbon was stirred in a hydrogen atmosphere until uptake ceased after 4.5 hours. After the usual workup, the crude product was triturated with hexane and filtered to give 0.45 g (87% yield, mp 71°–72°) of 3-(decyloxy)-5-[[6-(2,3-dihydroxyphenyl) hexyl]oxy]benzoic acid methyl ester.

Anal. Calcd for $C_{30}H_{44}O_6$: C, 71.97; H, 8.86. Found: C, 71.97; H, 9.03.

EXAMPLE 67

3-(Decyloxy)-5-[6-[[2,3-bis(phenylmethoxy)phenyl]hexyl]oxy]benzoic acid

A solution of 1.75 g (2.57 mmol) of 3-(decyloxy)-5-[[6-[2,3-bis (phenylmethoxy)phenyl]hexyl]oxy]benzoic acid methyl ester and 1.3 ml (7.8 mmol) of 6N NaOH in 75 ml of methanol and 25 ml of dioxane was stirred at reflux under argon for 24 hours. The usual workup gave 3-(decyloxy)-5-[[6-2,3-bis(phenylmethoxy)phenyl]hexyl]oxy]benzoic acid. The nmr and mass spectra were consistent with the structure.

EXAMPLE 68

3-(Decyloxy)-5-[[6-(2,3-dihydroxyphenyl)hexyl]oxy]benzoic acid

A mixture of 1.7 g of 3-(decyloxy)-5-[[6-[2,3-bis(phenylmethoxy) phenyl]hexyl]oxy]benzoic acid and 0.3 g of 10% palladium on carbon in 75 ml of THF was stirred in a hydrogen atmosphere until uptake ceased after 2.5 hours. The usual workup followed by trituration of the crude product from hexane and filtration gave 1.13 g (91% yield, mp 86°–88°) of 3-(decyloxy)-5-[[6-(2,3-dihydroxyphenyl)hexyl]oxy]benzoic acid.

Anal. Calcd for $C_{29}H_{42}O_6$: C, 71.58; H, 8.70. Found: C, 71.70; H, 8.72.

EXAMPLE 69

3-[[6-(2,3-Dihydroxyphenyl)hexyl]oxy]-5-(octadecyloxy) benzoic acid methyl ester A mixture of 0.15 g (0.25 mmol) of 3-[[6-(2,3-dihydroxyphenyl) hexyl]oxy]-5-(octadecyloxy)benzoic acid, 0.05 g (0.6 mmol) of sodium bicarbonate and 0.64 ml (10 mmol) of methyl iodide in 3 ml of DMF was stirred and heated at 40° for 5 days. An additional 0.32 ml of methyl iodide and 0.05 g of sodium bicarbonate were added and heating at 40° was continued for 6 days. The solvent was removed at reduced pressure, the residue was extracted with ethyl acetate and the extract was washed with water. The dried extract was concentrated to an oil which was purified by chromatography on 4 g of silica gel using 25% ethyl acetate-hexane to give 0.104 g (68% yield, mp 82°–84°) of 3-[[6-(2,3-dihydroxyphenyl)hexyl]oxy]-5-(octadecyloxy)benzoic acid methyl ester.

Anal. Calcd for $C_{36}H_{60}O_6$: C, 74.47; H, 9.87. Found: C, 74.35: H, 9.82.

EXAMPLE 70

3-[3-(4-Hydroxyphenoxy)propoxy]-5-(octadecyloxy) benzoic acid methyl ester

A mixture of 0.30 g (0.54 mmol) of 3-[3-(4-hydroxyphenoxy) propoxy]-5-(octadecyloxy)benzoic acid, 0.14 g (1.62 mmol) of sodium bicarbonate and 0.67 ml (10.8 mmol) of methyl iodide in 5 ml of DMF was stirred and heated at 40° for 48 hours. The solvent was removed at reduced pressure, the residue was extracted with ethyl acetate and the extract was washed with water. The dried extract was concentrated to a solid which was triturated with hexane and filtered to give 0.298 g (97% yield, mp 88°–90°) of 3-[3-(4-hydroxyphenoxy)propoxy]-5-(octadecyloxy)benzoic acid methyl ester.

Anal. Calcd for $C_{35}H_{54}O_6$: C, 73.63; H, 9.54. Found: C, 73.44; H, 9.45.

EXAMPLE 71

3-(Decyloxy)-5-[[6-(2,3-dihydroxyphenyl)hexyl]oxy]benzoic acid 2-(diethylamino)ethyl ester monohydrochloride salt To 0.5 g (0.75 mmol) of 3-(decyloxy)-5-[[6-[2,3-bis(phenylmethoxy)phenyl]hexyl]oxy]benzoic acid in 20 ml of DMF stirred under argon and heated at 80° was added dropwise a solution of 0.2 g (1.5 mmol) of 2-diethylaminoethyl chloride in 5 ml of DMF. The reaction mixture was stirred and heated at 80° for 3 hours when an additional 0.2 g of 2-diethylaminoethyl chloride was added. Heating was continued at 80° for 45 hours and the solvent was then removed at reduced pressure. Saturated $NaHCO_3$ solution was added to the residue and the product was extracted with ethyl acetate. The dried extract was concentrated to a yellow oil which was purified by chromatography on 40 g of 230–400 mesh silica gel using 50% ethyl acetate-hexane to give 0.25 g (44% yield) of 3-(decyloxy)-5-[[6-[2,3-bis(phenylmethoxy)phenyl]hexyl]oxy]benzoic acid 2-(diethylamino) ethyl ester as an oil. A mixture of 0.25 g of 3-(decyloxy)-5-[[6-[2,3-bis(phenylmethoxy)phenyl]hexyl]oxy]benzoic acid 2-(diethylamino) ethyl ester and 0.1 g of 10% palladium on carbon in 15 ml of THF was stirred at room temperature under a hydrogen atmosphere for 5 hours when uptake ceased. The usual workup gave the free base of the title compound which was dissolved in methylene chloride and treated with 0.32 ml of 3N HCl in ethanol. The solvents were removed at reduced pressure, the residue was triturated with ether and the product was removed by filtration to give 0.13 g, mp 88°–91°, of 3-(decyloxy)-5-[[6-(2,3-dihydroxyphenyl)hexyl]oxy]benzoic acid 2-(diethylamino)ethyl ester monohydrochloride salt.

Anal. Calcd for $C_{35}H_{55}NO_6 \cdot 1{:}1$ HCl: C, 67.56; H, 9.07; N, 2.25; $Cl^-$, 5.70. Found: C, 67.57; H, 8.94; 2.17; $Cl^-$ 5.50.

EXAMPLE 72

3-(Decyloxy)-5-[[6-(2,3-dihydroxyphenyl)hexyl]oxy]-benzoic acid (acetyloxy)methyl ester A mixture of 0.5 g (0.75 mmol) of 3-(decyloxy)-5-[[6-[2,3-bis (phenylmethoxy)phenyl]hexyl]oxy]benzoic acid, 0.25 g (2.25 mmol) of chloromethyl acetate, 0.23 g (1.5 mmol) of sodium iodide and 0.31 ml (2.25 mmol) of triethylamine in 15 ml of acetone and 5 ml of DMF was stirred at reflux under argon for 19 hours. The solvent was removed under reduced pressure, $NaHCO_3$ solution was added to the residue and the product was extracted with ethyl acetate. The dried extract was concentrated to an oil which was purified by HPLC using 10% ethyl acetate-hexane to give 0.13 g of 3-(decyloxy)-5-[[6-[2,3-bis(phenylmethoxy)phenyl]hexyl]oxy]benzoic acid (acetyloxy)methyl ester as an oil. A mixture of 0.13 g of 3-(decyloxy)-5-[[6-[2,3-bis (phenylmethoxy)-phenyl]hexyl]oxy]benzoic acid (acetyloxy)methyl ester and 0.1 g of 10% palladium on carbon in 15 ml of ethyl acetate was stirred under a hydrogen atmosphere for 3.5 hours when uptake ceased. The usual workup gave 0.07 g of 3-(decyloxy)-5-[[6-(2,3-dihydroxyphenyl)hexyl]oxy]benzoic acid (acetyloxy) methyl ester as an oil. The structure was confirmed by the nmr and mass spectra.

EXAMPLE 73
TABLET FORMULATION (Wet Granulation)

| Item | Ingredients | 5 mg | 10 mg | 25 mg | 100 mg | 250 mg | 500 mg |
|---|---|---|---|---|---|---|---|
| 1. | Compound A* | 5 | 10 | 25 | 100 | 250.0 | 500 |
| 2. | Lactose Anhydrous DTG | 125 | 120 | 105 | 30 | 75.0 | 150 |
| 3. | Pregelatinized Starch | 6 | 6 | 6 | 6 | 15.0 | 30 |
| 4. | Microcrystalline Cellulose | 30 | 30 | 30 | 30 | 75.0 | 150 |
| 5. | Magnesium Stearate | 1 | 1 | 1 | 1 | 2.5 | 5 |
|  | Total | 167 | 167 | 167 | 167 | 417.5 | 835 |

*3-[[6-(2,3-dihydroxyphenyl)hexyl]oxy]-5-(octadecyloxy)benzoic acid

EXAMPLE 74
TABLET FORMULATION (Wet Granulation)

| Item | Ingredients | 5 mg | 10 mg | 25 mg | 100 mg | 250 mg | 500 mg |
|---|---|---|---|---|---|---|---|
| 1. | Compound A* | 5 | 10 | 25 | 100 | 250.0 | 500 |
| 2. | Corn Starch | 103 | 98 | 83 | 8 | 20.0 | 403.3 |
| 3. | Modified Starch | 4 | 4 | 4 | 4 | 10.0 | 20 |
| 4. | Talc | 4 | 4 | 4 | 4 | 10.0 | 20 |
| 5. | Magnesium Stearate | 1 | 1 | 1 | 1 | 2.5 | 5 |
|  | Total | 117 | 117 | 117 | 117 | 292.5 | 585 |

EXAMPLE 75
o/w Cream, 5%

| Ingredients | % by Wt. |
|---|---|
| Compound A | 5.0 |
| Petrolatum (and) Lanolin (and) Lanolin Alcohol | 5.0 |
| Isodecyl Oleate | 1.0 |
| Octyl Palmitate | 1.0 |
| Disopropyl Adipate | 1.0 |
| Cetearyl Alcohol (and) Ceteareth 20 (Promulgen D) | 5.0 |
| Cetyl Alcohol | 1.0 |
| Stearyl Alcohol | 1.0 |
| Steareth —10 (Brij 76) | 1.0 |
| Steareth —20 (Brij 78) | 1.0 |
| Purified Water | 74.0 |
| Preservatives | q.s. |

1. Heat the petrolatum, lanolin, and lanolin alcohol mixture isodecyl oleate, octyl palmitate, diisopropyl adipate, cetearyl alcohol and ceteareth 20 mixture, cetyl alcohol, stearyl alcohol, steareth —10 and steareth 20° to 70°–80° C. Mix until all components have melted and are dissolved.
2. Heat the purified water to 70°–80° C. Add water soluble preservatives to the heated water and mix until dissolved.
3. Add the oil soluble preservatives to the lipid phase (Step 1). Mix until dissolved.
4. Dissolve the drug in the lipid phase from Step 3. Mix vigorously until the drug is dissolved.
5. Add Step 2 to Step 4. Homogenize until a uniform emulsion is formed.
6. Continue stirring the emulsion and cool to room temperature.

EXAMPLE 76
Hydrophilic Ointment 5%

| Ingredients | % by Wt. |
|---|---|
| Compound A | 5.0 |
| Petrolatum (and) Lanolin Alcohol (Amerchol CAB) | 10.0 |
| Isopropyl Lanolate (Amerlate P) | 5.0 |
| Petrolatum | 25.0 |
| Cetyl Alcohol | 2.0 |
| Stearyl Alcohol | 2.0 |
| Steareth —10 (Brij —76) | 2.0 |
| Steareth —20 (Brij —78) | 2.0 |
| Methyl Gluceth —20 (Glucam E-20) | 5.0 |
| Purified Water | 42.0 |
| Preservatives | q.s. |

1. Heat the petrolatum and lanolin alcohol mixture isopropyl lanolate, petrolatum, cetyl alcohol, stearyl alcohol, steareth —10, steareth —20 and methyl glyceth —20° to 70°, 80° C. Mix until all components have melted and are dissolved.
2. Heat the purified water to 70°–80° C. Add water soluble preservatives to the heated water and mix until dissolved.
3. Add the oil soluble preservatives to the lipid phase of Step 1. Mix until dissolved.

4. Dissolve the drug in the lipid phase from Step 3. Mix vigorously until the drug is dissolved.
5. Add Step 2 to Step 4. Homogenize until a uniform emulsion is formed.
6. Continue stirring the emulsion and cool to room temperature.

EXAMPLE 77
Ointment (Anhydrous) 5.0%

| Ingredients | % by wt. |
| --- | --- |
| Compound A | 5.0 |
| White Petrolatum | 38.0 |
| Mineral Oil, 70 vis. | 10.0 |
| Sorbitan Sesquioleate (Arlacel 83) | 5.0 |
| Petrolatum (and) Lanolin Alcohol (Amerchol CAB) | 15.0 |
| Isopropyl Lanolate (Amerlate P) | 6.0 |
| Mineral Oil (and) Lanolin Alcohol (Amerchol L101) | 10.0 |
| Acetylated Lanolin (Modulan) | 10.0 |
| Paraffin Wax | 2.0 |
| Preservative | q.s. |

1. Heat white petrolatum, mineral oil, sorbitan sesquioleate, petrolatum and lanolin alcohol mixture, isopropyl lanolate, mineral oil and lanolin alcohol mixture, acetylated lanolin and paraffin wax to 70°–80° C. Mix until all components have melted and are dissolved.
2. Cool the mixture from Step 1 to 50° C. and add the preservatives. Mix until dissolved.
3. Add the drug to Step 2. Mix vigorously until drug is dissolved.
4. Cool Step 3 to room temperature with stirring.

We claim:

1. A compound of the formula

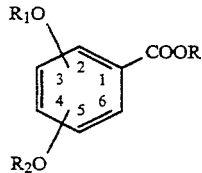

R is hydrogen, lower alkyl, —(CH$_2$)$_2$N(R$_3$)$_2$ or —CH$_2$OOCR$_3$ wherein R$_3$ is lower alkyl;
R$_1$ is CH$_3$(CH$_2$)$_n$—, wherein n is 9–17, or R$_4$(CH$_2$)$_p$—, wherein p is 3–10 and R$_4$ is 1- or 2-naphthyloxy, 2,3- or 3,4-dihydroxyphenyl, phenyl, phenoxy, or substituted phenyl or phenoxy wherein the substituent is selected from the group consisting of hydroxy, benzloxy, methylsulfinyl, methylsulfonyl or phenyl;
R$_2$ is R$_4$(CH$_2$)$_p$—, 1-adamantyl—CO— or diphenylmethyl—CO—, and, where R is hydrogen or a pharmaceutically acceptable salt with a base.

2. A compound, in accordance with claim 1, wherein the substitution pattern is:

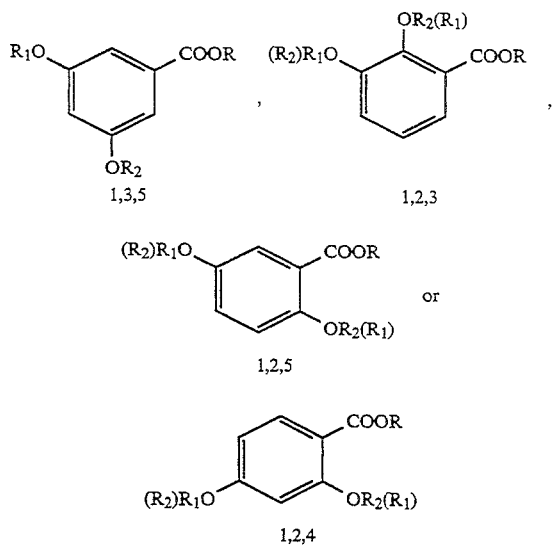

3. A compound in accordance with claim 1, wherein the substitution pattern is 1,3,5 or 1,2,3;
R$_1$ is CH$_3$(CH$_2$)$_n$—, wherein n is 9–17;
R$_2$ is 1-adamantyl—CO—, diphenylmethyl—CO—, or R$_4$(CH$_2$)$_p$—, wherein p is 3–10 and R$_4$ is 2,3- or 3,4-dihydroxyphenyl or substituted phenoxy wherein the substituent is selected from hydroxy or benzyloxy or methylsulfinyl.

4. A compound in accordance with claim 1, wherein the substitution pattern is 1,3,5;
R$_1$ is CH$_3$(CH$_2$)$_n$—, wherein n is 9–17;
R$_2$ is R$_4$(CH$_2$)$_p$—, wherein p is 3–8 and R$_4$ is 2,3-dihydroxyphenyl or substituted phenoxy wherein the substituent is selected from benzyloxy or hydroxy; and R is hydrogen.

5. A compound in accordance with claim 1, 3-[[6-(2,3-dihydroxyphenyl)hexyl]oxy]-5-(octadecyloxy)benzoic acid.

6. A compound in accordance with claim 1, 3-[3-(4-hydroxyphenoxy)propoxy]-5-(octadecyloxy)benzoic acid.

7. A compound in accordance with claim 1, 3-[3-(4-hydroxyphenoxy)propoxy]-5-(tetradecyloxy)benzoic acid.

8. A compound in accordance with claim 1, 3-(decyloxy)-5-[3-(4-hydroxyphenoxy)propoxy]benzoic acid.

9. A compound in accordance with claim 1, 3-[[6-(2,3-dihydroxyphenyl)hexyl]oxy]-5-(tetradecyloxy)-benzoic acid.

10. A compound in accordance with claim 1, 3-(decyloxy)-5-[[6-(2,3-dihydroxyphenyl)hexyl]oxy]benzoic acid.

11. A pharmaceutical composition comprising a compound of the formula

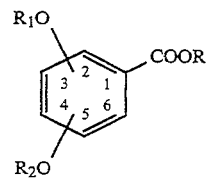

R is hydrogen, lower alkyl, —$(CH_2)_2N(R_3)_2$ or —$CH_2OOCR_3$ wherein $R_3$ is lower alkyl;

$R_1$ is $CH_3(CH_2)_n$—, wherein n is 9–17, or $R_4(CH_2)_p$—, wherein p is 2–18 and $R_4$ is 1- or 2-naphthyloxy, 2,3- or 3,4-dihydroxyphenyl, phenyl, phenoxy, or substituted phenyl or phenoxy wherein the substituent is selected from the group consisting of hydroxy, benzyloxy, methylsulfinyl, methylsulfonyl or phenyl;

$R_2$ is $R_4(CH_2)_p$—, 1-adamantyl—CO— or diphenylmethyl—CO—, and, when R is hydrogen or a pharmaceutically acceptable salt thereof with a base and an inert carrier.

12. A pharmaceutical composition, in accordance with claim 11, wherein the compound of formula I has the substitution pattern:

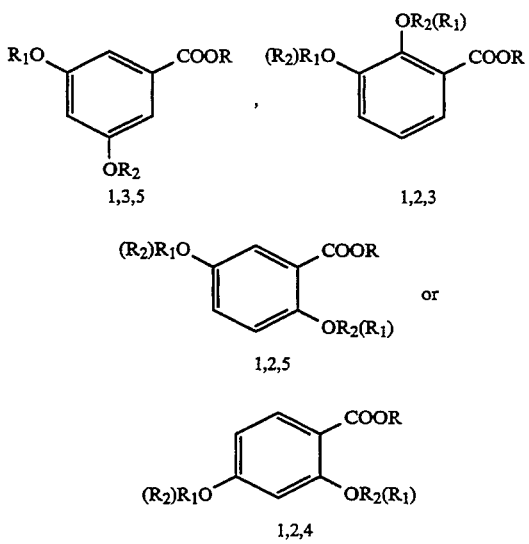

13. A pharmaceutical composition, in accordance with claim 11, wherein the compound of formula I has the substitution pattern of 1,3,5 or 1,2,3;

$R_1$ is $CH_3(CH_2)_n$—, wherein n is 9–17;

$R_2$ is 1-adamantyl—CO—, diphenylmethyl—CO—, or $R_4(CH_2)_p$—, wherein p is 3–10 and $R_4$ is 2,3- or 3,4-dihydroxyphenyl or substituted phenoxy wherein the substituent is selected from hydroxy or benzyloxy or methylsulfinyl and R is as defined.

14. A pharmaceutical composition, in accordance with claim 11, wherein the compound of formula I has the substitution pattern of 1,3,5;

$R_1$ is $CH_3(CH_2)_n$—, wherein n is 9–17;

$R_2$ is $R_4(CH_2)_p$—, wherein p is 3–8 and $R_4$ is 2,3-dihydroxyphenyl or substituted phenoxy wherein the substituent is selected from benzyloxy, hydroxy, nitro or amino; and R is hydrogen.

15. A pharmaceutical composition in accordance with claim 11, 3-[[6-(2,3-dihydroxyphenyl)hexyl]oxy]-5-(octadecyloxy)benzoic acid.

16. A pharmaceutical composition in accordance with claim 11, 3-[3-(4-hydroxyphenoxy)propoxy]-5-(octadecyloxy)benzoic acid.

17. A pharmaceutical composition in accordance with claim 11, 3-[3-(4-hydroxyphenoxy)propoxy]-5-(tetradecyloxy)benzoic acid.

18. A pharmaceutical composition in accordance with claim 11, 3-(decyloxy)-5-[3-(4-hydroxyphenoxy)-propoxy]benzoic acid.

19. A pharmaceutical composition in accordance with claim 11, 3-[[6-(2,3-dihydroxyphenyl)hexyl]oxy]-5-(tetradecyloxy)benzoic acid.

20. A method of inhibiting phospholipases $A_2$ which comprises administering to a host requiring such treatment an effective amount of a compound of the formula

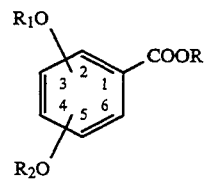

R is hydrogen, lower alkyl, —$(CH_2)_2N(R_3)_2$ or —$CH_2OOCR_3$ wherein $R_3$ is lower alkyl;

$R_1$ is $CH_3(CH_2)_n$—, wherein n is 9–17, or $R_4(CH_2)_p$—, wherein p is 3–10 and $R_4$ is 1- or 2-naphthyloxy, 2,3- or 3,4-dihydroxyphenyl, phenyl, phenoxy, or substituted phenyl or phenoxy wherein the substituent is selected from the group consisting of hydroxy, benzyloxy, methylsulfinyl, methylsulfonyl or phenyl;

$R_2$ is $R_4(CH_2)_p$—, 1-adamantyl—CO— or diphenylmethyl—CO—, and, when R is hydrogen or a pharmaceutically acceptable salt with a base.

21. A method of treating psoriasis which comprises administering to a host requiring such treatment an effective amount of a compound of the formula

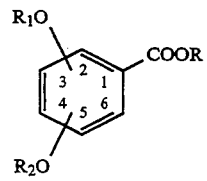

R is hydrogen, lower alkyl, —$(CH_2)_2N(R_3)_2$ or —$CH_2OOCR_3$ wherein $R_3$ is lower alkyl;

$R_1$ is $CH_3(CH_2)_n$—, wherein n is 9–17, or $R_4(CH_2)_p$—, wherein p is 3–10 and $R_4$ is 1- or 2-naphthyloxy, 2,3- or 3,4-dihydroxyphenyl, phenyl, phenoxy, or substituted phenyl or phenoxy wherein the substituent is selected from the group consisting of hydroxy, benzyloxy, methylsulfinyl, methylsulfonyl or phenyl;

$R_2$ is $R_4(CH_2)_p$—, 1-adamantyl—CO— or diphenylmethyl—CO—, and, when R is hydrogen or a pharmaceutically acceptable salt with a base.

22. A method of treating dermatitis which comprises administering to a host requiring such treatment an effective amount of a compound of the formula

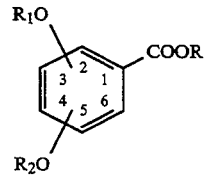

R is hydrogen, lower alkyl, —$(CH_2)_2N(R_3)_2$ or —$CH_2OOCR_3$ wherein $R_3$ is lower alkyl;

$R_1$ is $CH_3(CH_2)_n$—, wherein n is 9–17, or $R_4(CH_2)_p$—, wherein p is 3–10 and $R_4$ is 1- or 2- naphthyloxy, 2,3- or 3,4-dihydroxyphenyl, phenyl, phenoxy, or substituted phenyl or phenoxy wherein the substituent is selected from the group consisting of hydroxy, benzyloxy, methylsulfinyl, methylsulfonyl or phenyl;

$R_2$ is $R_4(CH_2)_p$—, 1-adamantyl—CO— or diphenylmethyl—CO—, and, when R is hydrogen or a pharmaceutically acceptable salt thereof with a base.

23. A method, in accordance with claim 20, wherein the compound of formula 1 has the substitution pattern:

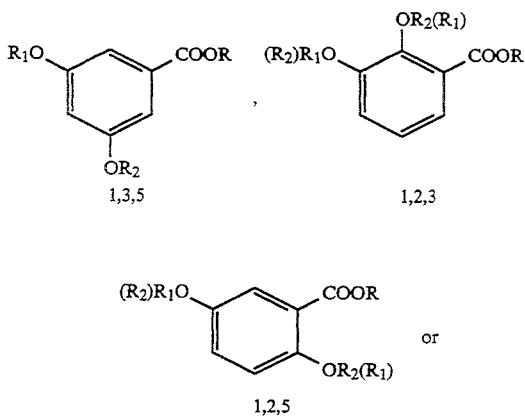

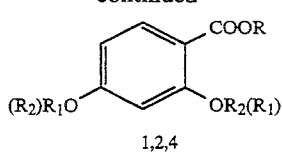

24. A method, in accordance with claim 20, wherein the compound of formula 1 has the substitution pattern of 1,3,5 or 1,2,3;
$R_1$ is $CH_3(CH_2)_n$—, wherein n is 6-17;
$R_2$ is 1-adamantyl—CO—, diphenylmethyl—CO—, or $R_4(CH_2)_p$—, wherein p is 3-10 and $R_4$ is 2,3- or 3,4-dihydroxyphenyl or substituted phenoxy wherein the substituent is selected from hydroxy, benzyloxy, methoxy, nitro, amino or methylsulfinyl.

25. A method, in accordance with claim 20, wherein the compound of formula I has the substitution pattern of 1,3,5;
$R_1$ is $CH_3(CH_2)_n$—, wherein n is 9-17; $R_2$ is $R_4(CH_2)_p$—, wherein p is 3-8 and $R_4$ is 2,3-dihydroxyphenyl or substituted phenoxy wherein the substituent is benzyloxy or hydroxy; and R is hydrogen.

26. A method in accordance with claim 20, 3-[[6-(2,3-dihydroxyphenyl)hexyl]oxy]-5-(octadecyloxy)benzoic acid.

27. A method in accordance with claim 20, 3-[3-(4-hydroxyphenoxy)propoxy]-5-(octadecyloxy)benzoic acid.

28. A method in accordance with claim 20, 3-[3-(4-hydroxyphenoxy)propoxy]-5-(tetradecyloxy)benzoic acid.

29. A method in accordance with claim 20, 3-(decyloxy)-5-[3-(4-hydroxyphenoxy)propoxy]benzoic acid.

30. A method in accordance with claim 20, 3-[[6-(2,3-dihydroxyphenyl)hexyl]oxy]-5-(tetradecyloxy)benzoic acid.

* * * * *